United States Patent [19]
Bagley et al.

[11] Patent Number: 5,334,598
[45] Date of Patent: Aug. 2, 1994

[54] SIX-MEMBERED RING FUSED IMIDAZOLES SUBSTITUTED WITH PHENOXYPHENYLACETIC ACID DERIVATIVES

[75] Inventors: Scott W. Bagley, Groton, Conn.; Prasun K. Chakravarty, Edison; Anna Chen, Rahway; Daljit S. Dhanoa, Secaucus Falls; Kenneth J. Fitch, Cranford; William J. Greenlee, Teaneck; Elizabeth M. Naylor, Scotch Plains; Thomas F. Walsh, Westfield, all of N.J.; David L. Williams, Jr., Telford, Pa.

[73] Assignee: Merck & Co., Inc., Rahway, N.J.

[21] Appl. No.: 35,340

[22] Filed: Mar. 19, 1993

[51] Int. Cl.⁵ .................. A61K 31/435; C07D 471/04
[52] U.S. Cl. ...................... 514/303; 514/81; 514/256; 514/234.2; 544/127; 544/333; 546/23; 546/118
[58] Field of Search ................ 546/118, 23; 514/303, 514/81, 234.2, 256; 544/127, 333

[56] References Cited

U.S. PATENT DOCUMENTS

| | | | |
|---|---|---|---|
| 5,082,838 | 1/1992 | Naka et al. | 514/211 |
| 5,114,918 | 5/1992 | Ishikawa et al. | 514/11 |
| 5,177,095 | 1/1993 | Greenlee et al. | 514/384 |
| 5,183,810 | 2/1993 | Greenlee et al. | 514/63 |
| 5,187,195 | 2/1993 | Oohata et al. | 514/510 |

FOREIGN PATENT DOCUMENTS

| | | |
|---|---|---|
| 2073841 | 1/1993 | Canada . |
| 0436189A1 | 7/1990 | European Pat. Off. . |
| 0457195A2 | 11/1991 | European Pat. Off. . |
| 0460679A2 | 12/1991 | European Pat. Off. . |
| 0496452A1 | 7/1992 | European Pat. Off. . |
| 0510526A1 | 10/1992 | European Pat. Off. . |
| 0526642A1 | 2/1993 | European Pat. Off. . |
| 0526708A1 | 2/1993 | European Pat. Off. . |
| WO91/11999 | 8/1991 | PCT Int'l Appl. . |
| WO92/15321 | 9/1992 | PCT Int'l Appl. . |
| WO92/20706 | 11/1992 | PCT Int'l Appl. . |
| 2259450A | 3/1993 | United Kingdom . |

*Primary Examiner*—Bernard Dentz
*Attorney, Agent, or Firm*—Valerie J. Camara; Mark R. Daniel; Joseph F. DiPrima

[57] ABSTRACT

Phenoxyphenylacetic acids and derivatives of general structural formula I have endothelin

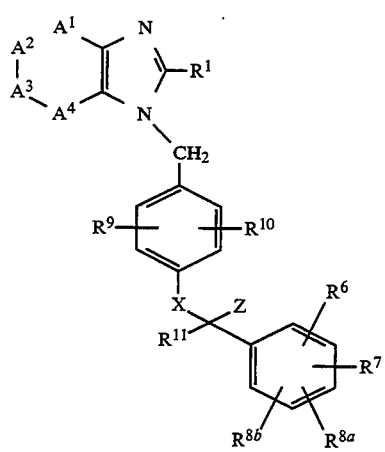

antagonist activity and are therefore useful in treating cardiovascular disorders, such as hypertension, congestive heart failure, postischemic renal failure, vasospasm, cerebral and cardiac ischemia, myocardial infarction, inflammatory diseases, Raynaud's disease, and endotoxic shock, and asthma.

8 Claims, No Drawings

SIX-MEMBERED RING FUSED IMIDAZOLES SUBSTITUTED WITH PHENOXYPHENYLACETIC ACID DERIVATIVES

SUMMARY OF THE INVENTION

This invention is concerned with non-peptidic endothelin receptor antagonists and their method of use. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1-3]

Endothelin-1 (ET-1) is one of three recently identified potent vasoconstricting peptides which also includes endothelin-2 (ET-2) and endothelin-3 (ET-3) which differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane A$_2$,[14] prostacyclin, norepinephrine, angiotensin II and substance P.[11-16] Further, endothelin causes contraction of the smooth muscle of the gastrointestinal tract and the uterine smooth muscle.[1,7-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that cyclosporin added to a renal cell culture, increased endothelin secretion.[24] Another study has shown that administration of cyclosporin to rats led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Substances which specifically inhibit the binding of endothelin to its receptor are believed to block the physiological effects of endothelin and would be useful in treating patients with endothelin related disorders. The present invention discloses potent non-peptidic endothelin antagonists. Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction.

The novel compounds of the present invention are useful as a non-peptidic endothelin antagonists, and have not been disclosed in any issued patents or patent applications. Fujisawa in European Patent Application EP 457,195, Banyu in EP 436,189 and 460,679, and Takeda in Patent Cooperation Treaty International Publication No. WO 91/13089 have applications disclosing linear and cyclic peptidic compounds as endothelin antagonists. Fujisawa has also disclosed anthraquinone derivatives produced by a fermentation process using Streptomyces sp. No. 89009 in EP 405,421.

A Roussel-Uclaf European Patent Application (EP 498,723) disclosed a series of substituted (1,4-quinolinoxy)methylbiphenylcarboxylic acids as both endothelin antagonists and angiotensin II antagonists. A patent from Hoffmann-La Roche (EP 510,526) has also appeared claiming the endothelin antagonist properties of a series of N-(4-pyrimidinyl)benzenesulfonamides.

REFERENCES

1 Nature, 332, 411–415 (1988).
2 FEBS Letters, 231, 440–444 (1988).
3 Biochem. Biophys. Res. Commun. 154, 868–875 (1988).
4 TiPS, 13, 103–108, March 1992.
5 Japan J. Hypertension 12, 79 (1989).
6 J. Vascular Medicine Biology, 2, 207 (1990).
7 J. Am. Med. Association, 264, 2868 (1990).
8 The Lancet, ii, 207 (1990) and The Lancet, ii, 747–748 (1989).
9 Japan. Soc. Cereb. Blood Flow & Metabol. 1, 73 (1989).
10 J. Clin. Invest., 83, 1762–1767 (1989).
11 Biochem. Biophys. Res. Comm. 157, 1164–1168 (1988).
12 Biochem. Biophys. Res. Comm. 155, 167–172 (1989).
13 Proc. Natl. Acad. Sci. USA, 85, 9797–9800 (1989).
14 J. Cardiovasc. Pharmacol., 13, 589–592 (1989).
15 Japan. J. Hypertension 12, 76 (1989).
16 Neuroscience Letters, 102, 179–184 (1989).
17 FEBS Letters, 247, 337–340 (1989).

18 Eur. J. Pharmacol. 154, 227–228 (1988).
19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

DETAILED DESCRIPTION OF THE INVENTION

This invention relates to compounds of the general Formula I useful in this novel method of treatment:

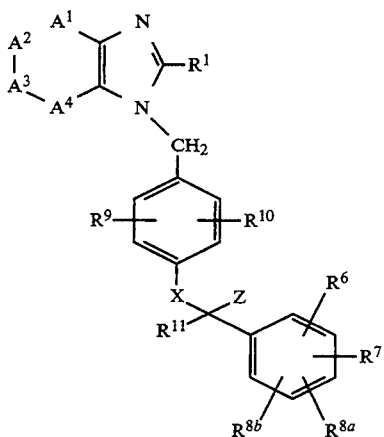

or a pharmaceutically acceptable salt thereof wherein:
$R^1$ is:
- (a) H,
- (b) $(C_1-C_6)$-alkyl, $(C_2-C_6)$-alkenyl or $(C_2-C_6)$-alkynyl each of which is unsubstituted or substituted with a substituent selected from the group consisting of:
  - i) phenyl or naphthyl as defined in $R^1(c)$,
  - ii) $(C_3-C_7)$-cycloalkyl,
  - iii) Cl, Br, I, F,
  - iv) OH,
  - v) $NH_2$,
  - vi) $NH(C_1-C_4)$-alkyl,
  - vii) $N[(C_1-C_4)\text{-alkyl}]_2$,
  - viii) $NHSO_2R^2$,
  - ix) $(C_1-C_4)$-perfluoroalkyl,
  - x) $COOR^2$, or
  - xi) $SO_2NHR^3$,
  - xii) $-S(O)_n-(C_1-C_4)$-alkyl, or
  - xiii) $-O-(C_1-C_4)$-alkyl,
- (c) aryl, wherein aryl is defined as phenyl or naphthyl which is unsubstituted, mono- or disubstituted with substituents selected from the group consisting of:
  - i) Cl, Br, I, F,
  - ii) $(C_1-C_4)$-alkyl,
  - iii) $(C_1-C_4)$-alkoxy,
  - iv) $NO_2$,
  - v) $CF_3$,
  - vi) $SO_2NR^3R^3$,
  - vii) $(C_1-C_4)$-alkylthio,
  - viii) hydroxy,
  - ix) amino,
  - x) $(C_3-C_7)$-cycloalkyl, or
  - xi) $(C_3-C_{10})$-alkenyl,
- (d) heteroaryl, wherein heteroaryl is defined as a 5- or 6-membered heteroaromatic moiety selected from the group consisting of thiophene, furan, thiazole, oxazole, pyridine or pyrimidine, which is unsubstituted, mono- or disubstituted with substituents selected from the group consisting of:
  - i) Cl, Br, I, F,
  - ii) OH,
  - iii) SH,
  - iv) $NO_2$,
  - v) $(C_1-C_4)$-alkyl,
  - vi) $(C_2-C_4)$-alkenyl,
  - vii) $(C_2-C_4)$-alkynyl,
  - viii) $(C_1-C_4)$-alkoxy, or
  - ix) $CF_3$,
- (e) $(C_1-C_4)$-perfluoroalkyl,
- (f) $-O-(C_1-C_6)$-alkyl,
- (g) $-S(O)_n-(C_1-C_4)$-alkyl,
- (h) $-CONR^3R^3$,
- (i) $-NR^3CO-O(C_1-C_4)$-alkyl, or
- (j) $(C_3-C_7)$-cycloalkyl; and $-A^1-A^2-A^3-A^4-$ is:

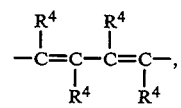 (a)

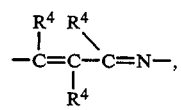 (b)

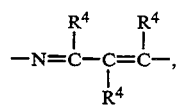 (c)

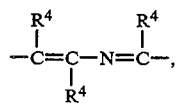 (d)

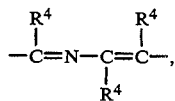 (e)

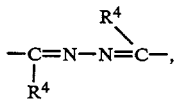 (f)

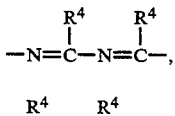 (g)

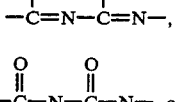 (h)

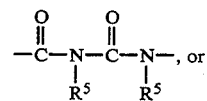 (i)

-continued

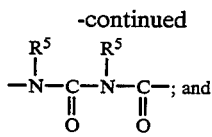

n is: 0 to 2; and
R² is:
  (a) H, or
  (b) (C₁–C₆)-alkyl; and
R³ is:
  (a) R²,
  (b) benzyl, or
  (c) phenyl; and
R⁴ groups are independently:
  (a) H,
  (b) (C₁–C₆)-alkyl or (C₂–C₆)-alkenyl each of which is unsubstituted or substituted with one of the following substituents,
    i) —OH,
    ii) —O-(C₁–C₄)-alkyl,
    iii) —S(O)$_n$-(C₁–C₄)-alkyl,
    iv) —NR⁵-(C₁–C₄)-alkyl,
    v) —NHR⁵,
    vi) —COOR⁵,
    vii) —CONHR⁷,
    ix) —CONR⁵R¹³, or
    x) (C₃–C₇)-cycloalkyl,
  (c) (C₃–C₇)-cycloalkyl,
  (d) F, Cl, Br, I,
  (e) CF₃,
  (f) —COOR⁵,
  (g) —CONR⁵R¹³,
  (h) —NR⁵R¹³,
  (i) —NR⁵CONR⁵R¹³,
  (j) —NR⁵COOR¹³,
  (k) —SO₂NR⁵R¹³,
  (l) —O-(C₁–C₄)-alkyl,
  (m) —S(O)$_n$-(C₁–C₄)-alkyl, or
  (n) —NHSO₂R¹³; and
R⁵ is:
  (a) H,
  (b) (C₁–C₆)-alkyl,
  (c) aryl, wherein aryl is phenyl or naphthyl, which is unsubstituted or substituted as defined in R¹(c),
  (d) —CH₂-aryl, wherein aryl is phenyl or naphthyl, which is unsubstituted or substituted as defined in R¹(c), or
  (e) (C₃–C₇)-cycloalkyl; and
R⁶, R⁷, R⁸ᵃ and R⁸ᵇ are independently:
  (a) H,
  (b) F, Cl, Br, or I,
  (c) —NO₂,
  (d) —NH₂,
  (e) —NH(C₁–C₄)-alkyl,
  (f) —N[(C₁–C₄)-alkyl]₂,
  (g) —SO₂NHR⁵,
  (h) —CF₃,
  (i) (C₁–C₄)-alkyl,
  (j) —OR⁵,
  (k) —S(O)$_n$-(C₁–C₄)-alkyl,
  (l) —NHCO-(C₁–C₄)-alkyl,
  (m) —NHCO—O(C₁–C₄)-alkyl,
  (n) —CH₂O-(C₁–C₄)-alkyl,
  (o) —O-(CH₂)m-OR⁵,
  (p) —CONR⁵R¹³, or
  (q) —COOR⁵; and m is 2, 3, or 4; and
R⁶ and R⁷ on adjacent carbon atoms can be joined together to form a ring structure:

A ;

A represents:
  a) —Y—C(R⁴)=C(R⁴)—,
  b) —Y—C(R⁴)=N—,
  c) —Y—N=C(R⁴)—,
  d) —Y—[C(R¹²)(R¹²)]$_s$—Y—,
  e) —Y—C(R¹²)(R¹²)—C(R¹²)(R¹²)—,
  f) —C(R⁴)=C(R⁴)—Y—,
  g) —N=C(R⁴)—Y—,
  h) —C(R¹²)(R¹²)—C(R¹²)(R¹²)—Y—, or
  i) —C(R⁴)=C(R⁴)—C(R⁴)=C(R⁴)—; and
s is 1 or 2; and
Y is —O—, —S(O)$_n$— and NR⁵; and
R⁹ and R¹⁰ are independently:
  (a) H,
  (b) (C₁–C₆)-alkyl, unsubstituted or substituted with (C₃–C₇)-cycloalkyl,
  (c) (C₂–C₆)-alkenyl,
  (d) (C₂–C₆)-alkynyl,
  (e) Cl, Br, F, I,
  (f) (C₁–C₆)-alkoxy,
  (g) when R⁹ and R¹⁰ are on adjacent carbons, they can be joined to form a phenyl ring,
  (h) perfluoro-(C₁–C₆)-alkyl,
  (i) (C₃–C₇)-cycloalkyl, unsubstituted or substituted with (C₁–C₆)-alkyl,
  (j) aryl, wherein aryl is phenyl or naphthyl,
  (k) (C₁–C₆)-alkyl-S(O)$_n$—(CH₂)$_n$—,
  (l) hydroxy-(C₁–C₆)-alkyl or dihydroxy-(C₁–C₆)-alkyl,
  (m) —CF₃,
  (n) —CO₂R⁵,
  (o) —OH,
  (p) —NR⁵R¹³,
  (q) —[(C₁–C₆)-alkyl]NR⁵R¹³,
  (r) —NO₂,
  (s) —(CH₂)$_n$—SO₂—N(R⁵)₂,
  (t) —NR⁵CO—(C₁–C₄)-alkyl, or
  (u) —CON(R⁵)₂;
X is:
  (a) —O—,
  (b) —S(O)$_n$—,
  (c) —NR⁵—
  (d) —CH₂O—,
  (e) —CH₂S(O)$_n$,
  (f) —CH₂NR⁵—,
  (g) —OCH₂—,
  (h) —NR⁵CH₂—,
  (i) —S(O)$_n$CH₂—,
  (j) single bond, or
R¹¹ is:
  (a) H,
  (b) (C₁–C₆)-alkyl, unsubstituted or substituted with a substituent selected from the group consisting of:
    (i) -aryl, wherein aryl is phenyl or naphthyl,
    (ii) -(C₃–C₇)-cycloalkyl,
    (iii) —NR⁵R¹³,
    (iv) -morpholin-4-yl, (v) —OH,
(vi) —CO$_2$R$^5$, or
(vii) —CON(R$^5$)$_2$,
(c) aryl, wherein aryl is phenyl or naphthyl, which is unsubstituted or substituted with a substituent selected from the group consisting of:
  i) (C$_1$-C$_4$)-alkyl,
  ii) —O—(C$_1$-C$_4$)-alkyl,
  iii) —CONR$^5$R$^{13}$,
  iv) F, Cl, Br or I, or
  v) —COOR$^5$;

R$^{12}$ is:
(a) H,
(b) (C$_1$-C$_4$)-alkyl unsubstituted or substituted with one of the following substituents:
  i) —OH,
  ii) —NR$^5$R$^{13}$,
  iii) —COOR$^5$,
  iv) —CONHR$^5$, or
  v) —CONR$^5$R$^{13}$;

Z is:
(a) —CO$_2$H,
(b) —CO$_2$R$^{14}$,
(c) -tetrazol-5-yl,
(d) —CONH(tetrazol-5-yl)
(e) —CONHSO$_2$-phenyl or —CONHSO$_2$-naphthyl, wherein phenyl or naphthyl is unsubstituted or substituted as defined in R$^1$(c),
(f) —CONHSO$_2$-(C$_1$-C$_8$)-alkyl, wherein the alkyl group is unsubstituted or substituted with a substituent selected from the group consisting of: —OH, —SH, —O(C$_1$-C$_4$)-alkyl, —S—(C$_1$-C$_4$)-alkyl, —CF$_3$, Cl, Br, F, I, —NO$_2$, —CO$_2$H, —CO$_2$-(C$_1$-C$_4$)-alkyl, —NH$_2$, —NH[(C$_1$-C$_4$)-alkyl], or —N[(C$_1$-C$_4$)-alkyl]$_2$,
(g) —CONHSO$_2$-(C$_1$-C$_4$)-perfluoroalkyl,
(h) —CONHSO$_2$-heteroaryl, wherein heteroaryl is as defined in R$^1$(d),
(i) —CONHSO$_2$NR$^3$R$^3$,
(j) —SO$_2$NHCO-phenyl or —SO$_2$NHCO-naphthyl, wherein phenyl or naphthyl is unsubstituted or substituted as defined in R$^1$(c),
(k) —SO$_2$NHCO-(C$_1$-C$_8$)-alkyl, wherein the alkyl group is unsubstituted or substituted with a substituent selected from the group consisting of: —OH, —SH, —O(C$_1$-C$_4$)-alkyl, —S-(C$_1$-C$_4$)-alkyl, —CF$_3$, Cl, Br, F, I, —NO$_2$, —CO$_2$H, —CO$_2$-(C$_1$-C$_4$)-alkyl, —NH$_2$, —NH[(C$_1$-C$_4$)-alkyl], or —N[(C$_1$-C$_4$)-alkyl]$_2$,
(l) —SO$_2$NHCO-(C$_1$-C$_4$)-perfluoroalkyl,
(m) —SO$_2$NHCO-heteroaryl, wherein heteroaryl is as defined in R$^1$(d),
(n) —SO$_2$CONR$^3$R$^3$,
(o) —PO(OH)$_2$,
(p) —PO(OR$^2$)$_2$, or
(q) —PO(OH)(OR$^2$); and R$^{13}$ is:
(a) H,
(b) (C$_1$-C$_6$)-alkyl,
(c) allyl,
(d) (C$_3$-C$_6$)-cycloalkyl,
(e) (C$_1$-C$_4$)-acyl,
(f) benzyl, or
(g) phenyl; and R$^{14}$ is:
(a) (C$_1$-C$_4$)-alkyl,
(b) CHR$^{15}$—O—COR$^{16}$,
(c) CH$_2$CH$_2$—N[(C$_1$-C$_2$)-alkyl]$_2$,
(d) CH$_2$CH$_2$—N[CH$_2$CH$_2$]$_2$O,
(e) (CH$_2$CH$_2$O)$_y$-O—[(C$_1$-C$_4$)-alkyl], wherein y is 1 or 2,
(f) phenyl, naphthyl, CH$_2$-phenyl or CH$_2$-naphthyl, where phenyl or naphthyl is substituted or unsubstituted with CO$_2$-(C$_1$-C$_4$)-alkyl,

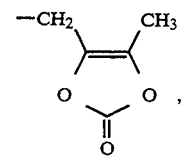

(g)

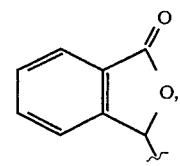

(h)

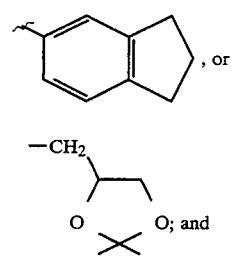

(i), or

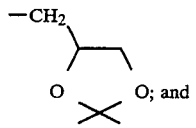

(j)

R$^{15}$ and R$^{16}$ independently are (C$_1$-C$_6$)-alkyl or phenyl.

Wherein a preferred embodiment is when:

R$^1$ is:
(a) H,
(b) (C$_1$-C$_6$)-alkyl, (C$_2$-C$_6$)-alkenyl or (C$_2$-C$_6$)-alkynyl each of which is unsubstituted or substituted with a substituent selected from the group consisting of:
  i) (C$_3$-C$_5$)-cycloalkyl,
  ii) —O-(C$_1$-C$_4$)-alkyl,
  iii) —S-(C$_1$-C$_4$)-alkyl,
  iv) CF$_3$, or
  v) CF$_2$CF$_3$,
(c) (C$_1$-C$_4$)-perfluoroalkyl,
(d) —O-(C$_1$-C$_6$)-alkyl,
(e) —S(O)$_n$-(C$_1$-C$_6$)-alkyl,
(f) —CONR$^3$R$^3$, or
(g) —NR$^3$CO—O(C$_1$-C$_4$)-alkyl;

—A$^1$—A$^2$—A$^3$—A$^4$— is:

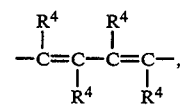

(a)

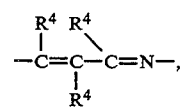

(b)

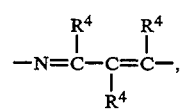

(c)

-continued

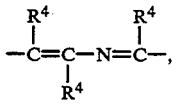 (d)

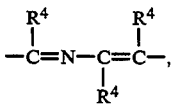 (e)

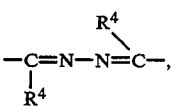 (f)

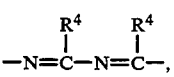 (g)

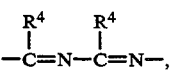 (h)

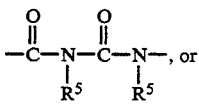 (i)

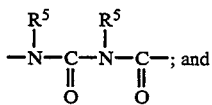 (j)

n is: 0, 1, or 2; and
$R^2$ is:
(a) H, or
(b) $(C_1-C_6)$-alkyl; and
$R^3$ is:
(a) $R^2$,
(b) benzyl, or
(c) phenyl; and
$R^4$ groups are independently:
(a) H,
(b) $(C_1-C_6)$-alkyl which is unsubstituted or substituted with one of the following substituents,
   i) —OH,
   ii) —O-$(C_1-C_4)$-alkyl,
   iii) —S(O)$_n$-$(C_1-C_4)$-alkyl,
   iv) —NR$^5$-$(C_1-C_4)$-alkyl,
   v) —NHR$^5$,
   vi) —COOR$^5$,
   vii) —CONHR$^5$,
   viii) —OCOR$^{13}$,
   ix) —CONR$^5$R$^{13}$, or
   x) $(C_3-C_7)$-cycloalkyl,
(c) $(C_3-C_7)$-cycloalkyl,
(d) F, Cl, Br, I,
(e) $CF_3$,
(f) —COOR$^5$,
(g) —CONR$^5$R$^{13}$,
(h) —NR$^5$R$^{13}$,
(i) —NR$^5$CONR$^5$R$^{13}$,
(j) —NR$^5$COOR$^{13}$, or
(k) —O-$(C_1-C_4)$-alkyl; and
$R^5$ is:
(a) H,
(b) $(C_1-C_6)$-alkyl,
(c) phenyl, or
(d) benzyl; and $R^6$, $R^7$, $R^{8a}$ and $R^{8b}$ are independently:
(a) H,
(b) F, Cl, Br, or I,
(c) —NO$_2$,
(d) $(C_1-C_4)$-alkyl,
(e) —OR$^5$,
(f) —S(O)$_n$-$(C_1-C_4)$-alkyl,
(g) —NHCO-$(C_1-C_4)$-alkyl,
(h) —NHCO—O$(C_1-C_4)$-alkyl,
(i) —O—(CH$_2$)m-OR$^5$,
(j) —CONR$^5$R$^{13}$, or
(k) —COOR$^5$; and
m is 2, 3, or 4; and
$R^6$ and $R^7$ on adjacent carbon atoms can be joined together to form a ring structure:

A ;

A represents:
a) —Y—C(R$^4$)=C(R$^4$)—,
b) —Y—C(R$^4$)=N—,
c) —Y—N=C(R$^4$)—,
d) —Y—[C(R$^{12}$)(R$^{12}$)]$_s$—Y—,
e) —Y—C(R$^{12}$)(R$^{12}$)—C(R$^{12}$)(R$^{12}$)—,
f) —C(R$^4$)=C(R$^4$)—Y—,
g) —N=C(R$^4$)—Y—,
h) —C(R$^{12}$)(R$^{12}$)—C(R$^{12}$)(R$^{12}$)—Y—, or
i) —C(R$^4$)=C(R$^4$)—C(R$^4$)=C(R$^4$)—; and
s is 1 or 2; and
Y is —O—, —S(O)$_n$— and NR$^5$; and
$R^9$ and $R^{10}$ are independently:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxy, or
(e) hydroxy-$(C_1-C_6)$-alkyl or dihydroxy-$(C_1-C_6)$-alkyl; and
X is:
(a) —O—,
(b) —S(O)$_n$—, or
(c) —NR$^5$—; and
$R^{11}$ is:
(a) H,
(b) $(C_1-C_6)$-alkyl, unsubstituted or substituted with:
   (i) -aryl, wherein aryl is phenyl or naphthyl,
   (ii) -$(C_3-C_7)$-cycloalkyl,
   (iii) —NR$^5$R$^{13}$,
   (iv) -morpholin-4-yl,
   (v) —OH,
   (vi) —CO$_2$R$^5$, or
   (vii) —CON(R$^5$)$_2$,
(c) aryl, wherein aryl is phenyl or naphthyl, which is unsubstituted or substituted with a substituent selected from the group consisting of:
   i) $(C_1-C_4)$-alkyl,
   ii) —O-$(C_1-C_4)$-alkyl,
   iii) —CONR$^5$R$^{13}$,
   iv) F, Cl, Br or I, or
   v) —COOR$^5$;
$R^{12}$ is:
(a) H, (b) (C$_1$-C$_4$)-alkyl unsubstituted or substituted with one of the following substituents:
  i) —OH,
  ii) —NR$^5$R$^{13}$,
  iii) —COOR$^5$,
  iv) —CONHR$^5$, or
  v) —CONR$^5$R$^{13}$;

Z is:
  (a) —CO$_2$H,
  (b) —CO$_2$R$^{14}$,
  (c) -tetrazol-5-yl,
  (d) —CONH(tetrazol-5-yl)
  (e) —CONHSO$_2$-phenyl or —CONHSO$_2$-naphthyl, wherein phenyl or naphthyl is unsubstituted or substituted as defined in R$^1$(c),
  (f) —CONHSO$_2$-(C$_1$-C$_8$)-alkyl, wherein the alkyl group is unsubstituted or substituted with a substituent selected from the group consisting of: —OH, —SH, —O(C$_1$-C$_4$)-alkyl, —S-(C$_1$-C$_4$)-alkyl, —CF$_3$, Cl, Br, F, I, —NO$_2$, —CO$_2$H, —CO$_2$-(C$_1$-C$_4$)-alkyl, —NH$_2$, —NH[(C$_1$-C$_4$)-alkyl], or —N[(C$_1$-C$_4$)-alkyl]$_2$,
  (g) —CONHSO$_2$-(C$_1$-C$_4$)-perfluoroalkyl,
  (h) —CONHSO$_2$-heteroaryl, wherein heteroaryl is as defined in R$^1$(d),
  (i) —CONHSO$_2$NR$^3$R$^3$,
  (j) —SO$_2$NHCO-phenyl or —SO$_2$NHCO-naphthyl, wherein phenyl or naphthyl is unsubstituted or substituted as defined in R$^1$(c),
  (k) —SO$_2$NHCO-(C$_1$-C$_8$)-alkyl, wherein the alkyl group is unsubstituted or substituted with a substituent selected from the group consisting of: —OH, —SH, —O(C$_1$-C$_4$)-alkyl, —S-(C$_1$-C$_4$)-alkyl, —CF$_3$, Cl, Br, F, I, —NO$_2$, —CO$_2$H, —CO$_2$-(C$_1$-C$_4$)-alkyl, —NH$_2$, —NH[(C$_1$-C$_4$)-alkyl], or —N[(C$_1$-C$_4$)-alkyl]$_2$,
  (l) —SO$_2$NHCO-(C$_1$-C$_4$)-perfluoroalkyl,
  (m) —SO$_2$NHCO-heteroaryl, wherein heteroaryl is as defined in R$^1$(d),
  (n) —SO$_2$CONR$^3$R$^3$,
  (o) —PO(OH)$_2$,
  (p) —PO(OR$^2$)$_2$, or
  (q) —PO(OH)(OR$^2$); and R$^{13}$ is:
  (a) H,
  (b) (C$_1$-C$_6$)-alkyl,
  (c) allyl,
  (d) (C$_3$-C$_6$)-cycloalkyl,
  (e) (C$_1$-C$_4$)-acyl,
  (f) benzyl, or
  (g) phenyl; and R$^{14}$ is:
  (a) (C$_1$-C$_4$)-alkyl,
  (b) CHR$^{15}$—O—COR$^{16}$,
  (c) CH$_2$CH$_2$—N[(C$_1$-C$_2$)-alkyl]$_2$,
  (d) CH$_2$CH$_2$—N[CH$_2$CH$_2$]$_2$O,
  (e) (CH$_2$CH$_2$O)$_y$—O-[(C$_1$-C$_4$)-alkyl], wherein y is 1 or 2,
  (f) phenyl, naphthyl, —CH$_2$-phenyl or —CH$_2$-naphthyl, wherein phenyl or naphthyl is substituted or unsubstituted with CO$_2$-(C$_1$-C$_4$)-alkyl,

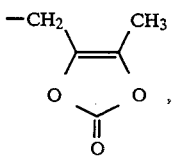
(g)

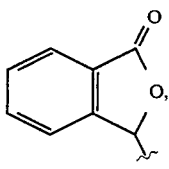
(h)

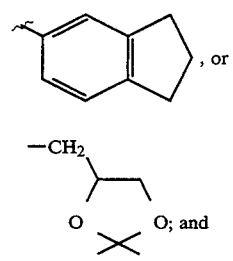
, or (i)

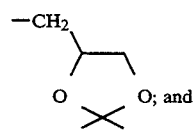
(j)
O; and

R$^{15}$ and R$^{16}$ independently are (C$_1$-C$_6$)-alkyl or phenyl.

A class of this embodiment of the invention is a compound of Formula II:

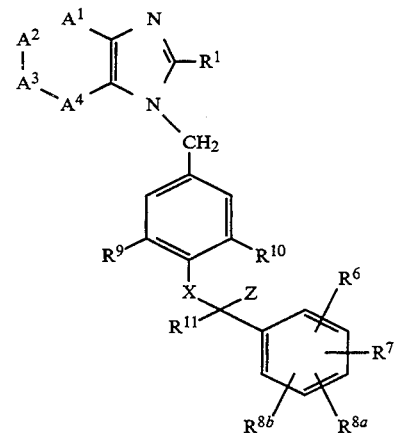

II wherein
R$^1$ is:
  (a) H,
  (b) (C$_1$-C$_6$)-alkyl,
  (c) (C$_1$-C$_4$)-perfluoroalkyl,
  (d) —O-(C$_1$-C$_6$)-alkyl, or
  (e) —S(O)$_n$-(C$_1$-C$_6$)-alkyl; and
—A$^1$—A$^2$—A$^3$—A$^4$— is:

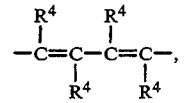
(a)

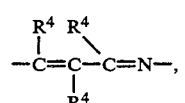
(b)

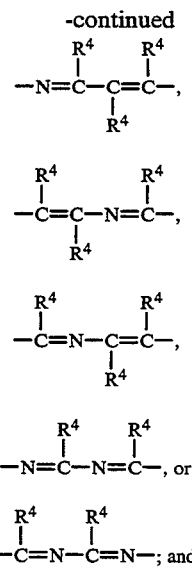

n is: 0, 1, or 2; and
R⁹ and R¹⁰ are each independently:
(a) $(C_1-C_6)$-alkyl,
(b) $(C_1-C_6)$-alkoxy,
(c) F, Cl, Br, I,
(d) $(C_1-C_6)$-alkyl-$(C_3-C_7)$-cycloalkyl, or
(e) hydroxy$(C_1-C_6)$-alkyl or dihydroxy$(C_1-C_6)$-alkyl; and X is:
(a) —O—, or
(b) $NR^5$;

Z is:
(a) —COOH,
(b) -tetrazol-5-yl,
(c) —CONH(5-tetrazolyl),
(d) —CONHSO$_2$-$(C_1-C_4)$-alkyl,
(e) —CONHSO$_2$-$(C_1-C_4)$-phenyl or —CONHSO$_2$-$(C_1-C_4)$-naphthyl, wherein phenyl or naphthyl is unsubstituted or substituted as defined in $R^1$(c), or
(f) —CONHSO$_2$-$(C_1-C_4)$-heteroaryl, wherein heteroaryl is as defined in $R^1$(d).

Another embodiment of the invention is a compound of Formula III:

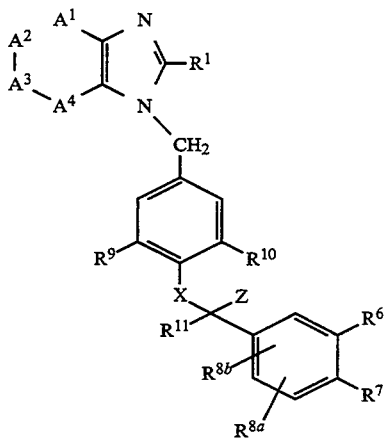

$R^1$ is:
(a) H,
(b) $(C_1-C_6)$-alkyl, or
(c) $(C_1-C_4)$-perfluoroalkyl; and
—A$^1$—A$^2$—A$^3$—A$^4$— is:

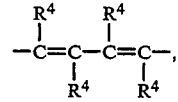

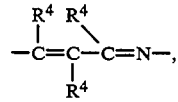

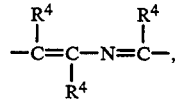

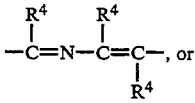

$$-\overset{R^4}{\underset{}{C}}=N-\overset{}{\underset{R^4}{C}}=N-;$$

$R^4$ groups are independently:
(a) H,
(b) $(C_1-C_6)$-alkyl,
(c) $(C_3-C_7)$-cycloalkyl,
(d) F, Cl, Br, I,
(e) $CF_3$,
(f) —COOR$^5$,
(g) —CONR$^5$R$^{13}$,
(h) —NR$^5$R$^{13}$,
(i) —NR$^5$CONR$^5$R$^{13}$,
(j) —NR$^5$COOR$^{13}$, or
(k) —O—$(C_1-C_4)$-alkyl; and $R^6$ and $R^7$ on adjacent carbon atoms can be joined together to form a ring structure:

A ;

A represents:
a) —O—C(R$^4$)=C(R$^4$)—,
b) —O—C(R$^4$)=N—,
c) —O—[C(R$^{12}$)(R$^{12}$)]$_s$—O—,
d) —C(R$^4$)=C(R$^4$)—O—,
e) —N=C(R$^4$)—O—, or
f) —C(R$^4$)=C(R$^4$)—C(R$^4$)=C(R$^4$)—; and
s is 1 or 2; and $R^{8a}$ and $R^{8b}$ are independently:
(a) H,
(b) F, Cl, Br, or I,
(c) —NO$_2$,
(d) $(C_1-C_4)$-alkyl,
(e) —OR$^5$,
(f) —S(O)$_n$-$(C_1-C_4)$-alkyl,
(g) —NHCO—$(C_1-C_4)$-alkyl,
(h) —NHCO—O$(C_1-C_4)$-alkyl,
(i) —O—(CH$_2$)$_m$-OR$^5$,
(j) —CONR$^5$R$^{13}$, or
(k) —COOR$^5$; and m is 2, 3, or 4; and
R$^{12}$ is:
(a) H, or
(b) (C$_1$–C$_4$)-alkyl.

The following Tables (I–V) further exemplify the scope of the invention described by formula II (wherein X is —O— and R$^7$, R$^{8a}$ and R$^{8b}$ are H, unless specified otherwise).

TABLE I

| R$^1$ | R$^{4a}$ | R$^{4b}$ | R$^9$ | R$^{10}$ | R$^6$, R$^7$, R$^{8a}$, R$^{8b}$ | Z |
|---|---|---|---|---|---|---|
| Pr | 4-Me | 7-Me | Me | Me | 3-OMe | COOH |
| Bu | 5-PhCO | H | Bu | H | 3-OMe | COOH |
| Ph | H | H | Pr | H | 3-OMe | COOH |
| Pr | H | H | Cl | H | 3-OMe | COOH |
| Bu | H | H | Br | Br | 3-OMe | COOH |
| Ph | H | H | Cl | Cl | 3-OMe | COOH |
| t-Bu | H | H | Pr | Pr | 3-OMe | COOH |
| Pr | H | H | Pr | Pr | 3-OMe | COOH |
| Bu | H | H | Pr | H | 4-OMe | COOH |
| Ph | H | H | Pr | Pr | 3-OMe | tetrazol-5-yl |
| Bu | H | H | Pr | Pr | 3-OMe | CONHSO$_2$Me |
| H | H | H | Pr | Pr | 3-OMe | COOH |
| H | H | H | Pr | Pr | 3,4-methylenedioxy | COOH |
| H | H | H | Pr | Pr | 2-OMe | COOH. |

TABLE II

| R$^1$ | R$^{4a}$ | R$^{4b}$ | R$^9$ | R$^{10}$ | R$^6$, R$^7$, R$^{8a}$, R$^{8b}$ | Z |
|---|---|---|---|---|---|---|
| Et | 5-Me | 7-Me | Pr | Pr | 2-Br,3-OMe,4-OMe,5-Br | COOH |
| H | H | 7-Me | Pr | Pr | 2-Br,3-OMe,4-OMe,5-Br | COOH |
| Et | 5-Me | 7-Me | Me | Me | 3-OMe | COOH |
| Pr | 6-PhCONH | H | Bu | H | 3-OMe | COOH |
| Et | 5-Me | 7-Me | Pr | H | 3-OM | COOH |
| Et | 5-Me | 7-Me | Cl | H | 3-OMe | COOH |
| Et | 5-Me | 7-Me | Br | Br | 3-OMe | COOH |
| Ph | H | H | Cl | Cl | 3-OMe | COOH |
| Me | H | H | Br | Br | 3-OMe | COOH |

TABLE II-continued

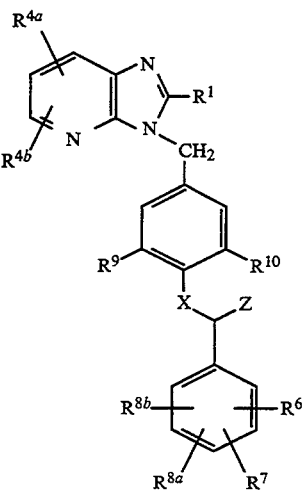

| $R^1$ | $R^{4a}$ | $R^{4b}$ | $R^9$ | $R^{10}$ | $R^6, R^7, R^{8a}, R^{8b}$ | Z |
|---|---|---|---|---|---|---|
| Et | 5-Me | 7-Me | Pr | Pr | 3-OMe | COOH |
| Et | 5-Me | 7-Me | Pr | Pr | 4-OMe | COOH |
| Et | 5-Me | 7-Me | Me | Me | 4-OMe | COOH |
| Et | 5-Me | 7-Me | Bu | H | 4-OMe | COOH |
| Bu | H | H | Cl | Cl | 4-OMe | COOH |
| Me | 5-Me | 7-Me | Br | Br | 4-OMe | COOH |
| Et | 5-Me | 7-Me | Pr | Pr | 2-OMe | COOH |
| Pr | 5-Me | 7-Me | Pr | H | 2-OMe | COOH |
| Pr | H | 7-Me | H | H | 2-OMe | COOH |
| Pr | 6-PhCONH | H | Bu | H | 2-OMe,4-OMe | COOH |
| Et | 5-Me | 7-Me | Cl | Cl | 2-OMe,4-OMe | COOH |
| Ph | H | H | Pr | Pr | 2-OMe,4-OMe | COOH |
| Et | 5-Me | 7-Me | Me | Me | 2-OMe,5-OMe | COOH |
| Ph | H | H | Cl | Cl | 2-OMe,5-OMe | COOH |
| Me | H | H | Br | Br | 3-OMe,4-OMe | COOH |
| Ph | H | H | Pr | Pr | 3-OMe,4-OMe | COOH |
| H | H | H | Pr | Pr | 3-OMe,4-OMe | COOH |
| Et | 5-Me | 7-Me | Pr | Pr | 3-OMe | $CONHSO_2Me$ |
| Me | 5-Me | 7-Me | Pr | Pr | 3-OMe | $CONHSO_2Ph$ |
| Et | 5-Me | 7-Me | Pr | Pr | 3-OMe,5-OMe | COOH |
| H | 5-Me | 7-Me | Pr | Pr | 3-OMe,5-OMe | COOH |
| Et | 5-Me | 7-Me | Pr | Pr | 3-OMe,5-OMe | $CONHSO_2Me$ |
| Et | 5-Me | 7-Me | Pr | Pr | 2-OMe,3-OMe | COOH |
| H | 5-Me | 7-Me | Pr | Pr | 2-OMe,3-OMe | COOH |
| Et | 5-Me | 7-Me | Pr | Pr | 2-OMe,3-OMe | $CONHSO_2Me$ |
| Et | H | 7-Me | Pr | Pr | 2,3-methylenedioxy | COOH |
| Et | H | 7-Me | Pr | Pr | 3,4-methylenedioxy | COOH |
| Et | 5-Me | 7-Me | Pr | Pr | 3,4-methylenedioxy | $CONHSO_2Me$ |
| Et | H | 7-Me | Pr | Pr | 3,4-methylenedioxy | COOH |
| H | H | 7-Me | Pr | Pr | 3,4-methylenedioxy | COOH |
| Me | H | H | Pr | Pr | 3,4-methylenedioxy | COOH |
| Me | H | H | Pr | Pr | 3-OMe,5-OMe | COOH |
| Et | Me | 6-NHCOPh | Pr | Pr | 3-OMe,5-OMe | COOH |
| H | H | 6-NHCOPh | Pr | Pr | 3-OMe,5-OMe | COOH |
| Et | 5-Me | 7-Me | H | Pr | 3,4-methylenedioxy | $CONHSO_2Ph(4\text{-}iPr)$ |
| Et | 5-Me | 7-Me | H | Pr | 3-OMe,5-OMe | $CONHSO_2Ph(4\text{-}iPr)$ |
| H | H | H | H | Pr | 3,4-methylenedioxy | $CONHSO_2Ph(4\text{-}iPr)$ |
| H | H | H | Pr | Pr | 5-Br,3,4-methylenedioxy | COOH |
| H | 5-Me | 7-Me | Pr | Pr | 5-Br,3,4-methylenedioxy | COOH |
| H | H | H | Pr | H | 5-Br,3,4-methylenedioxy | COOH |
| H | H | H | Pr | H | 5-Br,3,4-methylenedioxy | $CONHSO_2Ph(4\text{-}iPr)$ |
| Et | 5-Me | 7-Me | H | Pr | 3,4-methylenedioxy | $CONHSO_2Ph(4\text{-}tBu)$ |
| Et | 5-Me | 7-Me | H | —$CH_2$-c-Pr | 3,4-methylenedioxy | $CONHSO_2Ph(4\text{-}iPr)$ |
| H | H | H | H | Pr | 3,4-methylenedioxy | $CONHSO_2Ph(4\text{-}tBu)$ |
| H | H | H | H | —$CH_2$-c-Pr | 3,4-methylenedioxy | $CONHSO_2Ph(4\text{-}tBu)$. |

TABLE III

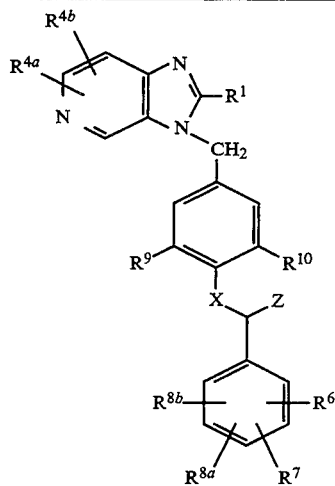

| $R^1$ | $R^{4a}$ | $R^{4b}$ | $R^9$ | $R^{10}$ | $R^6, R^7, R^{8a}, R^{8b}$ | Z |
| --- | --- | --- | --- | --- | --- | --- |
| Pr | 4-Me | 7-Me | Pr | H | 3-OMe | COOH |
| Ph | 4-Cl | H | Cl | H | 3-OMe | COOH |
| Ph | 4-Cl | H | Br | Br | 2-OMe | COOH |
| Me | 4-Cl | H | Pr | Pr | 2-OMe | COOH |
| Ph | 4-Me | H | Pr | Pr | 3-OMe | COOH |
| Me | 4-Cl | H | Pr | Pr | 4-OMe | COOH |
| Pr | 4-Me | H | Me | Me | 4-OMe | COOH |
| Ph | 4-Cl | H | Pr | Pr | 3-OMe,4-OMe | COOH |
| Ph | 4-Cl | H | Pr | Pr | 3-OMe,5-OMe | COOH |
| Et | 4-Me | H | Pr | H | 2-OMe | COOH |
| Ph | 4-Cl | H | Cl | Cl | 2-OMe,3-OMe | COOH |
| Me | 4-Cl | H | Br | Br | 2,3-methylenedioxy | COOH |
| Me | 4-Cl | H | Pr | Pr | 3,4-methylenedioxy | COOH |
| H | 4-Cl | H | Pr | Pr | 3,4-methylenedioxy | COOH |
| H | H | H | Pr | Pr | 3,4-methylenedioxy | COOH |
| H | H | H | Pr | Pr | 3-OMe,5-OMe | COOH |
| Et | 5-Me | 7-Me | H | Pr | 3,4-methylenedioxy | $CONHSO_2Ph(4\text{-}iPr)$ |
| Et | 5-Me | 7-Me | H | Pr | 3-OMe,5-OMe | $CONHSO_2Ph(4\text{-}iPr)$ |
| H | H | H | H | Pr | 3,4-methylenedioxy | $CONHSO_2Ph(4\text{-}iPr)$ |
| H | H | H | H | Pr | 3,4-methylenedioxy | $CONHSO_2Ph(4\text{-}tBu)$ |
| H | H | H | H | Pr | 3,4-methylenedioxy | $CONHSO_2Ph$ |
| H | H | H | H | Pr | 3-OMe,5-OMe | $CONHSO_2Ph(4\text{-}iPr)$ |
| Me | H | H | Pr | Pr | 3,4-methylenedioxy | COOH |
| Me | H | H | H | Pr | 3,4-methylenedioxy | COOH |
| Me | H | H | H | Pr | 3,4-methylenedioxy | $CONHSO_2Ph(4\text{-}iPr)$ |
| H | H | 7-SMe | Pr | Pr | 3,4-methylenedioxy | COOH |
| H | H | 7-NMe₂ | Pr | Pr | 3,4-methylenedioxy | COOH |
| H | H | H | Pr | Pr | 5-Br-3,4-methylenedioxy | COOH |
| Me | H | H | Pr | Pr | 5-Br-3,4-methylenedioxy | COOH. |

TABLE IV

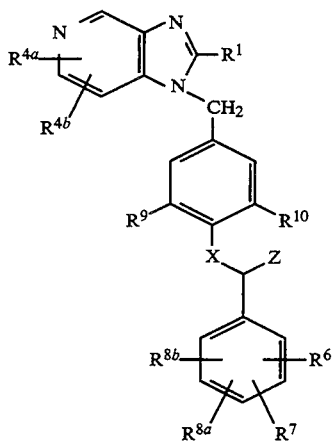

| $R^1$ | $R^{4a}$ | $R^{4b}$ | $R^9$ | $R^{10}$ | $R^6, R^7, R^{8a}, R^{8b}$ | Z |
| --- | --- | --- | --- | --- | --- | --- |
| Pr | 4-Me | 7-Me | Pr | H | 3-OMe | COOH |

TABLE IV-continued

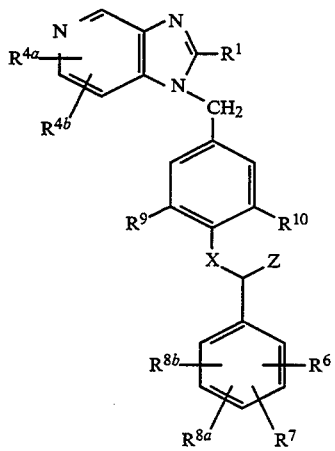

| R¹ | R$^{4a}$ | R$^{4b}$ | R⁹ | R¹⁰ | R⁶, R⁷, R$^{8a}$, R$^{8b}$ | Z |
|---|---|---|---|---|---|---|
| Ph | 4-Cl | H | Cl | H | 3-OMe | COOH |
| Ph | 4-Cl | H | Br | Br | 2-OMe | COOH |
| Me | 4-Cl | H | Pr | Pr | 2-OMe | COOH |
| Ph | 4-Me | H | Pr | Pr | 3-OMe | COOH |
| Me | 4-Cl | H | Pr | Pr | 4-OMe | COOH |
| Pr | 4-Me | H | Me | Me | 4-OMe | COOH |
| Ph | 4-Cl | H | Pr | Pr | 3-OMe,4-OMe | COOH |
| Ph | 4-Cl | H | Pr | Pr | 3-OMe,5-OMe | COOH |
| Et | 4-Me | H | Pr | H | 2-OMe | COOH |
| Ph | 4-Cl | H | Cl | Cl | 2-OMe,3-OMe | COOH |
| Me | 4-Cl | H | Br | Br | 2,3-methylenedioxy | COOH |
| Me | 4-Cl | H | Pr | Pr | 3,4-methylenedioxy | COOH |
| H | 4-Cl | H | Pr | Pr | 3,4-methylenedioxy | COOH |
| H | H | H | Pr | Pr | 3,4-methylenedioxy | COOH |
| H | H | H | Pr | Pr | 3-OMe,5-OMe | COOH |
| H | H | H | Pr | H | 3,4-methylenedioxy | CONHSO$_2$Ph(4-iPr). |

TABLE V

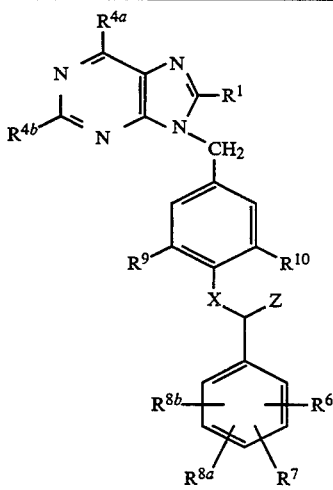

| R¹ | R$^{4a}$ | R$^{4b}$ | R⁹ | R¹⁰ | R⁶, R⁷, R$^{8a}$, R$^{8b}$ | Z |
|---|---|---|---|---|---|---|
| Me | N(Me)$_2$ | H | Pr | Pr | 3-OMe | COOH |
| Me | Me | Me | Pr | H | 3-OMe | COOH |
| Ph | H | H | Pr | Pr | 3-OMe | COOH |
| Bu | H | H | Pr | Pr | 4-OMe | COOH |
| Ph | Me | H | Me | Me | 2-OMe | COOH |
| Ph | Cl | H | Pr | Pr | 3-OMe,5-OMe | COOH |
| H | Cl | H | Pr | Pr | 3-OMe,5-OMe | COOH |
| H | Cl | H | Pr | Pr | 3,4-methylenedioxy | COOH |
| H | Cl | H | Pr | Pr | 2,3-methylenedioxy | COOH. |

The alkyl substituents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, furyl, pyrrolyl, thienyl, isothiazolyl, imidazolyl, pyrazinyl, pyrimidyl, pyrazolyl, purinyl, carbazolyl, isoxazolyl, thiazolyl, and oxazolyl.

Although the reaction schemes described below are reasonably general, it will be understood by those skilled in the art of organic synthesis that one or more functional groups present in a given compound of Formula I may render the molecule incompatible with a s particular synthetic sequence. In such a case an alternative synthetic route, an altered order of steps, or a strategy of protection and deprotection may be employed. In all cases the particular reaction conditions, including reagents, solvent, temperature and time, should be chosen so that they are consistent with the nature of the functionality present in the molecule.

The compounds of Formula I, and more specifically compounds where $R^{11}$ is hydrogen, can be synthesized using the reactions and techniques described for the synthesis of the non-heterocyclic components in the patent application WO91/11999 (Merck & Co.; published on Aug. 22, 1991 under the Patent Cooperation Treaty) and also U.S. Pat. No. 5,177,095 (Merck & Co.; Jan. 5, 1993).

The reaction schemes described below have been generalized for simplicity. It is further to be understood that in the generalized schemes below, unless specified more narrowly in the text, the alkyl and aryl groups represent unfunctionalized or functionalized derivatives as described before. The leaving group Q present in the alkylating agents is either chloro, bromo, iodo, methanesulfonate, p-toluenesulfonate or triflate.

Scheme 1

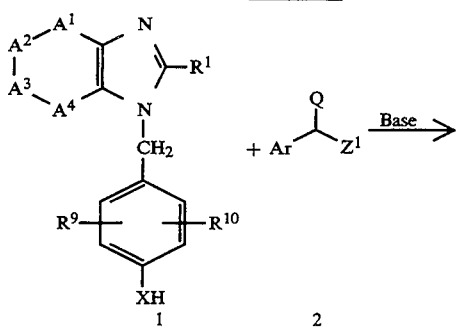

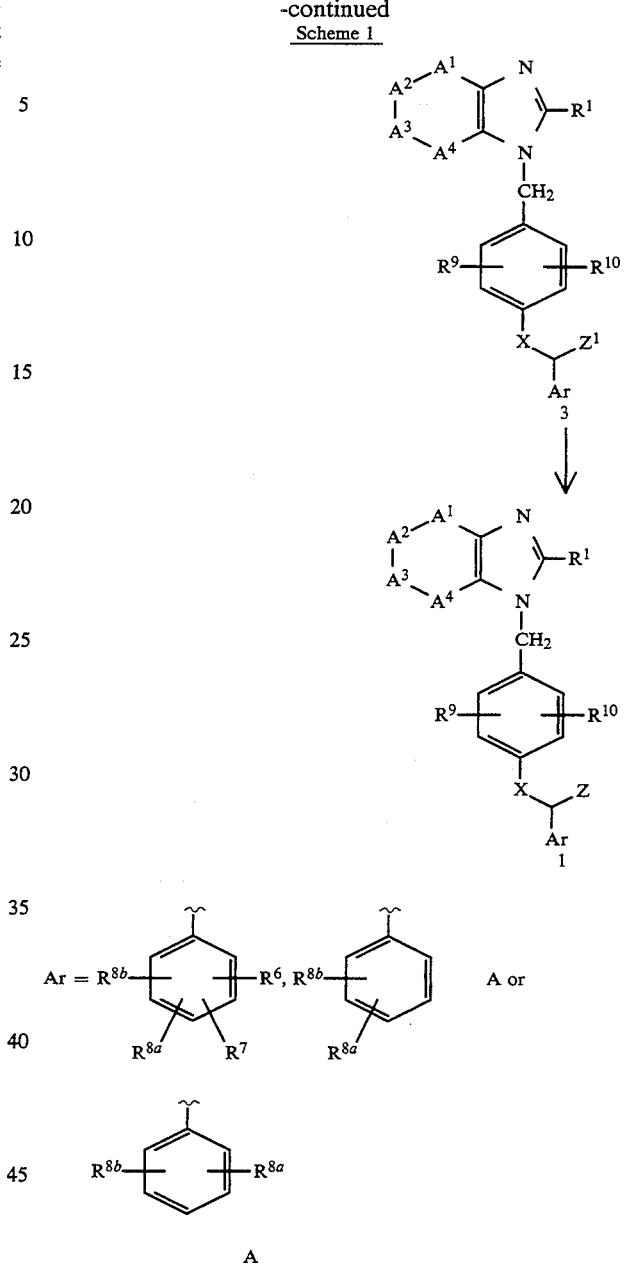

$Q$ = Cl, Br, I, OMs, OTs or OTf
$Z^1$ = a precursor to Z

More specifically, the compounds of Formula I (where X is oxygen, sulphur or appropriately substituted nitrogen and $R^{11}$ is H) can be synthesized as outlined in Scheme 1. The substituted compound 1 may be reacted with the alkylating agent 2 in an appropriate solvent such as alcohols (methanol, ethanol, isopropanol and like), dimethylformamide (DMF), dimethylsulfoxide (DMSO), tetrahydrofuran (THF) and acetone in the presence of an alkali metal salt such as alkoxides, carbonates, hydroxides and hydrides, or organic bases such as trialkylamines or alkyl lithiums to provide compound 3. The $Z^1$ group present in compound 3 may then be further transformed to provide desired compounds of Formula I.

In general, the alkylating agent 2 can be prepared using methods and techniques outlined in U.S. Pat. No.

5,177,095. More specifically, compound 2 (where $Z^1$ is COOR and Q is Br) can be synthesized from the substituted arylacetic acids 4 as outlined in Scheme 2. The substituted arylacetic acid 4 is converted to the corresponding ester either by refluxing the acid in an appropriate alcohol in the presence of a catalytic amount of conc. sulfuric acid, or using other conventional methods of esterification. The resulting ester is then refluxed in carbon tetrachloride with N-bromosuccinimide and a catalytic amount of a radical initiator (e.g., AIBN or benzoylperoxide) to provide the 2-bromo-arylacetic acid ester 5.

Scheme 2

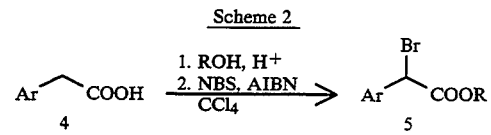

Alternatively, the ester 5 may also be prepared from appropriate aryl aldehydes (Scheme 3). The aldehyde 6 can be reacted with trimethylsilyl cyanide and catalytic amounts of KCN and 18-crown-6 to provide the corresponding trimethylsilyl cyanohydrin 7, which upon further treatment with the gaseous HCl and alcohol affords the 2-hydroxy ester 8. The ester 8 is treated with triphenylphosphine and carbon tetrabromide in methylene chloride to give the 2-bromoarylacetate derivatives 5.

Scheme 3

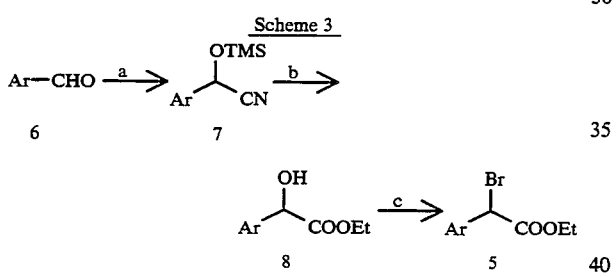

a. TMSCN, Cat. KCN, CH₂Cl₂, 18-Crown-6;
b. HCl (g), EtOH;
c. CBr₄, Ph₃P, CH₂Cl₂

Scheme 4 illustrates a typical synthesis of an alkylating agent 12 (where Ar represents substituted indoles). The appropriately substituted cyanoindole 9 (for a general synthesis of substituted indoles refer to, R. K. Brown, *Indoles, Part One*, Ed. W. J. Houlihan, Vol. 25, Chapter II, Wiley-Interscience, New York, 1972) is reduced with DIBALH to provide the corresponding aldehyde, which is then convened into the N-Boc derivative 10. Reaction of 10 with the trichloromethide anion [generated from KOH and CHCl₃; J. M. Wyvratt et. al., *J. Org. Chem.*, 52, 944–945 (1987)] followed by treatment with aqueous NaOH in DMF provides the alcohol 11. Treatment of 11 with diazomethane followed by the reaction with CBr₄/Ph₃P yields the alkylating agent 12.

A typical synthesis of alkylating agents bearing a substituted benzoxazole or benzthiazole ring is outlined in Scheme 5. The substituted benzoxazole 14 is prepared from the corresponding o-aminophenol 13 by the reaction of an appropriate orthoester under refluxing conditions (for other methods of synthesis of benzoxazoles see, S. A. Lang and Y. Lin, *Comprehensive Heterocyclic Chemistry*, Vol. 6, 1–130, Ed. C. W. Rees; and references cited therein). Reduction of 14 with NaBH₄ provides the alcohol 15 which is then subjected to pyridinium dichromate (PDC) oxidation to yield the corresponding aldehyde 16. Further elaboration of 16 as outlined provides the key intermediate 17. Similarly, the benzothiazole 19 can also be prepared form the appropriately substituted o-aminothiophenol 18.

Scheme 4

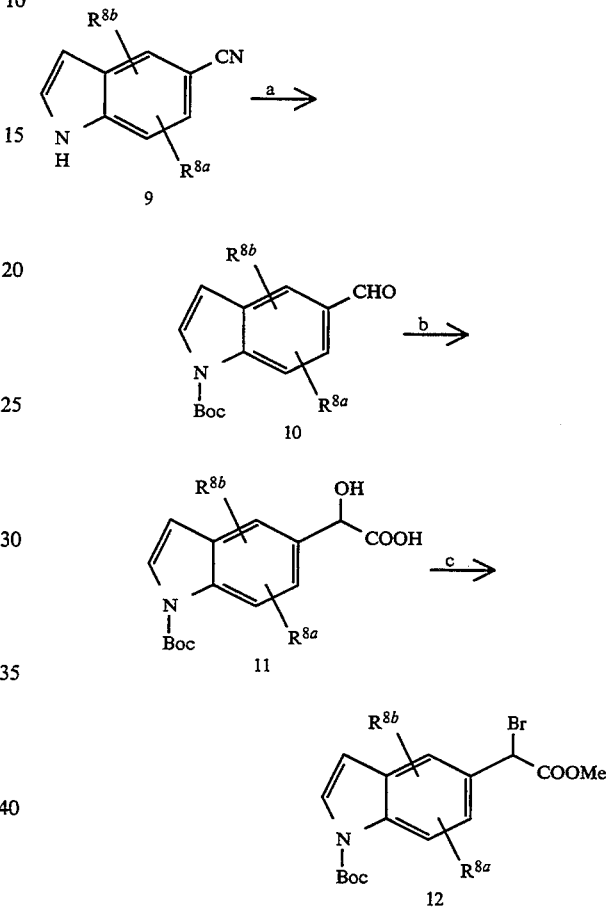

a. (i) DIBALH, Toluene; (ii) Boc₂O, DMAP, CH₂Cl₂
b. (i) CHCl₃, KOH, DMF, 0° C.; (ii) NaOH, DME/H₂O
c. (i) CH₂N₂; (ii) CBr₄/Ph₃P, CH₂Cl₂

Scheme 5

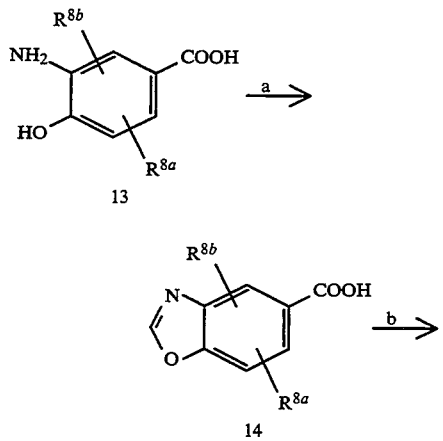

-continued
Scheme 5

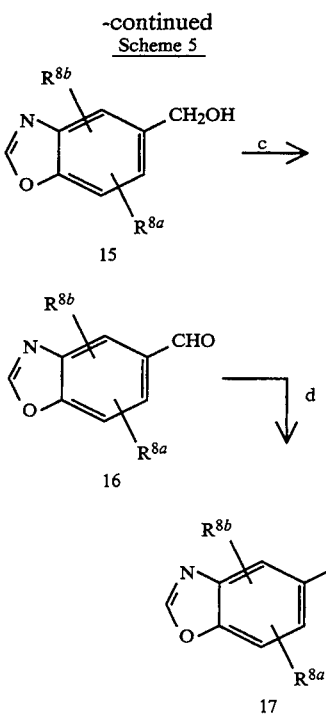

a. CH(OEt)₃, EtOH, reflux
b. (i) ClCOOEt, Et₃N, THF; (ii) NaBH₄, THF—H₂O
c. Pyridiniumdichromate, CH₂Cl₂
d. (i) CHCl₃, KOH, DMF, 0° C.; (ii) NaOH, DME/H₂O; (iii) HCl/MeOH; (iv) CBr₄/Ph₃P, CH₂Cl₂

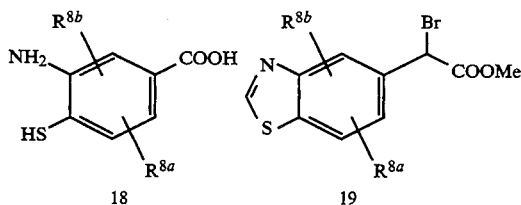

Scheme 6 illustrates the synthesis of benzofuran and dihydrobenzofuran alkylating agents 23 and 25. The benzofuran 21 can be prepared from the α-phenoxy carbonyl compound 20 via a ring closure reaction [Stoermer and Wehln, Chem. Ber., 35, 3549 (1902)] (for general methods of synthesis of benzofurans and dihydrobenzofurans see, R. C. Elderfield and V. B. Meyer, Heterocyclic Compounds, Vol. 2, Chapter 1, Ed. R. C. Elderfield, Wiley; and references cited therein). The ester 21 is reduced to provide the aldehyde 22 which is then transformed into the corresponding alkylating agent 23. The dihydrobenzofuran ester 24, obtained by catalytic reduction of 21, can also be transformed into the corresponding alkylating agent 25 using the sequence of reactions outlined in Scheme 6.

Benzothiophene 26 may be synthesized from the corresponding aldehyde 26b in a manner similar to that outlined in Scheme 6 for benzofuran 23. Benzothiophene 26b can be prepared by the oxidative cyclization (using an alkaline solution of potassium ferricyanide) of appropriately substituted o-mercaptocinnamic acid 26a [C. Chmelewsky and P. Friedlander, Chem. Ber., 46, 1903 (1913)]. (For general methods of synthesis of benzothiophene, See, E. Champaigne in Comprehensive Heterocyclic Chemistry, vol. 4, Chapter 3-15; Eds. A. Katritzky and C. W. Rees.)

Scheme 7 outlines a typical synthesis of an α-bromoarylacetates, 30 and 32, bearing appropriately substituted methylenedioxy or 1,4-dioxane rings. The substituted catechol derivative 27 is treated with an appropriate dibromide (where m is 1 or 2) in the presence of cesium carbonate in dimethylformamide to provide 28. Treatment of 28 with DIBALH yields the aldehyde 29 which is then transformed into the desired alkyl bromide as described.

Scheme 6

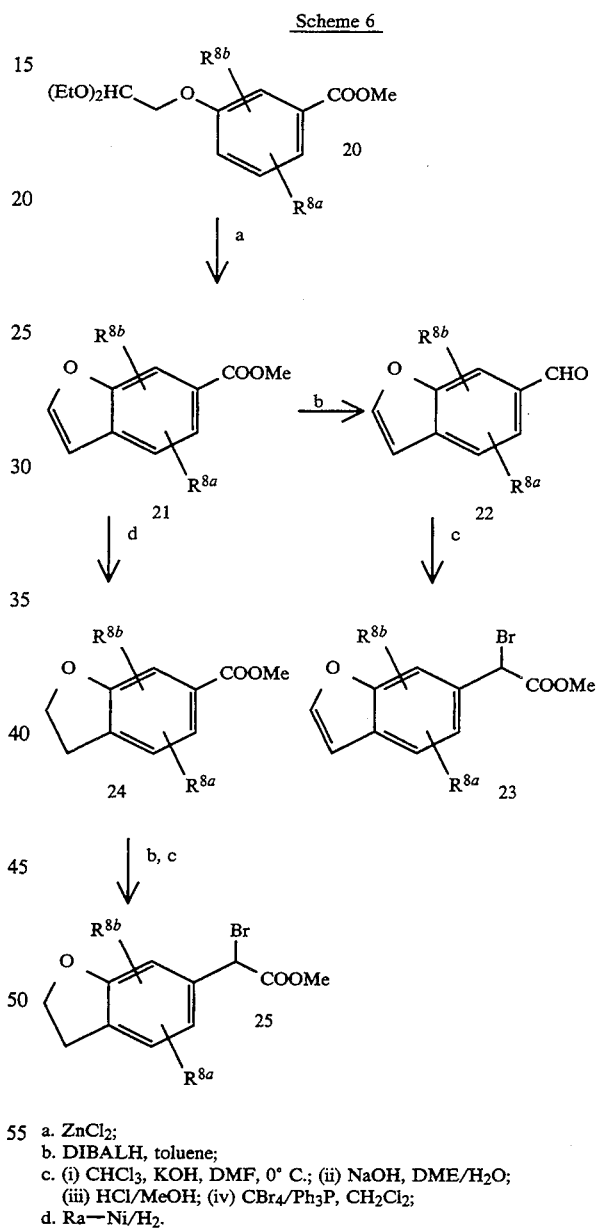

a. ZnCl₂;
b. DIBALH, toluene;
c. (i) CHCl₃, KOH, DMF, 0° C.; (ii) NaOH, DME/H₂O; (iii) HCl/MeOH; (iv) CBr₄/Ph₃P, CH₂Cl₂;
d. Ra—Ni/H₂.

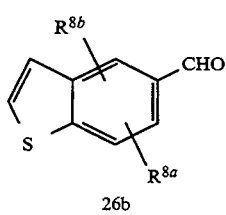

26b

29

-continued
Scheme 6

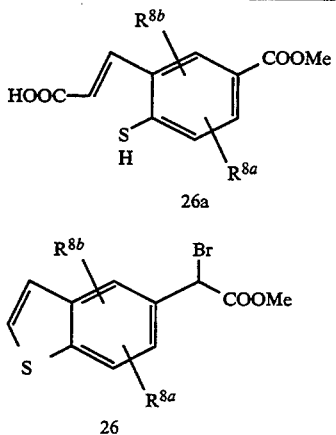

Scheme 7

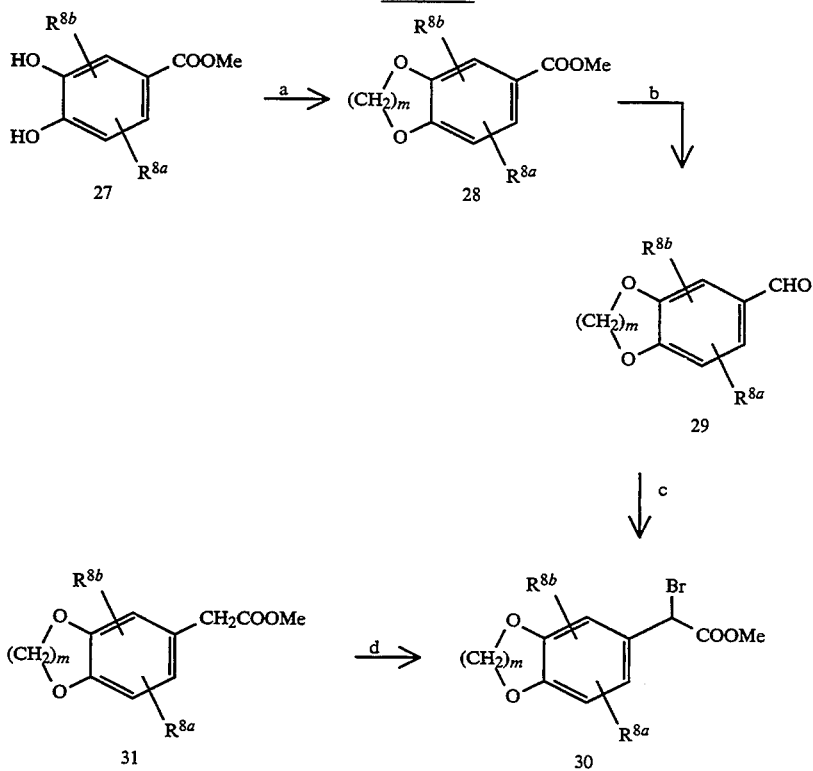

a. Br—(CH₂)ₘ—Br, Cs₂CO₃, DMF
b. DIBALH, toluene
c. (i) CHCl₃, KOH, DMF, 0° C.; (ii) NaOH, DME/H₂O;
   (iii) HCl/MeOH; (iv) CBr₄/Ph₃P, CH₂Cl₂;
d. NBS, AIBN, CCl₄

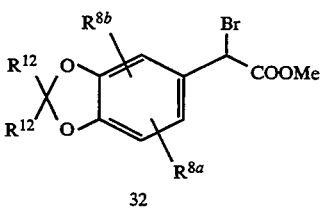

The compounds of Formula (I) can be synthesized using the reactions and techniques described in the International Application WO91/11999 published under the Patent Cooperation Treaty to (Merck & Co.) on Aug. 22, 1991.

The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The compounds useful in the novel method treatment of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H₂SO₄, H₃PO₄, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formula I in this invention may be derivatized at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306–326, H. Ferres, *Drugs of Today*, Vol 19, 499–538 (1983) and *J. Med. Chem.*, 18, 172 (1975)). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual enantiomers are considered to be in the scope of this invention. The racemic compounds of this invention may be resolved to provide individual enantiomers utilizing methods known to those skilled in the art of organic synthesis. For example, diastereoisomeric salts, esters or imides may be obtained from a racemic compound of general Formula I and a suitable optically active amine, amino acid, alcohol or the like. The diastereoisomeric salts, esters or imides are separated and purified, the optically active enantiomers are regenerated and the preferred enantiomer is the more potent isomer. The resolved enantiomers of the compounds of general Formula I, their pharmaceutically acceptable salts and their prodrug forms are also included within the scope of this invention.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to smooth muscle, neural and atrial sites, endothelin receptors may be found in gastrointestinal, kidney, lung, urogenital, uteral and placental tissues.

Endothelin is a potent vasoconstrictor peptide and thus plays an in vivo role in arterial pressure-volume homeostasis. Not only peripheral, but coronary vascular resistance as well, is increased by endothelin. Cardiac output is decreased, while plasma renin activity is increased. There is a reduction in renal blood flow and glomerular filtration rate, while levels of atrial natriuretic factor, vasopressin, and aldosterone become elevated.

It is also considered, in accordance with the present invention, that antagonists for the endothelin receptor may be useful in preventing or reducing restenosis subsequent to denudation following angioplasty. Such denudation results from myointimal thickening following angioplasty, which is caused by increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, the novel compounds of the present invention, which are receptor antagonists of endothelin, have therapeutic usefulness in preventing, decreasing or modulating the various physiological effects of endothelin discussed above, by wholly or partially blocking access of endothelin to its receptor.

Endothelin Receptor Binding Assays

The binding of the novel compound of this invention to the endothelin receptor was determined in accordance with the assay described in detail immediately below. It is similar to the assay described in Ambar et al. (1989) *Biochem. Biophys. Res. Commun.* 158, 195–201; and Kloog et al. (1989) *FEBS Letters*, 253, 199–202.

The endothelins (ETs) have a number of potent effects on a variety of cells, and exert their action by interacting with specific receptors present on cell membranes. The compound described in the present invention acts as an antagonist of ET at the receptors. In order to identify ET antagonists and determine their efficacy in vitro, the following three ligand receptor assays were established.

Receptor binding assay using cow aorta membrane preparation

Thoracic aortae were obtained from fleshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25M sucrose, 5 mM tris-HCl, pH 7.4, containing 0.5 µg/mL leupeptin and 7 µg/mL pepstatin A. Tissue was homogenized twice and then centrifuged for 10 minutes at 750×g at 4° C. The supernatant was filtered through cheesecloth and centrifuged again for 30 minutes at 48,000×g at 4° C. The membrane pellet thus obtained was resuspended in the buffer solution described above (including the protease inhibitors), and aliquots were quick-frozen and stored at −70° C. until use. Membranes were diluted into 50 mM KPi, 5 mM EDTA pH 7.5 containing 0.01% human serum albumin. Assays were done in triplicate. Test compounds and 100 pM [$^{125}$I]-endothelin-1 (2000–2200 Ci/µmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}I$ radioactivity in a gamma counter. Nondisplaceable binding of [$^{125}I$]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration ($IC_{50}$) which gives 50% displacement of the total specifically bound [$^{125}I$]-endothelin-1 was presented as a measure of the potency of such compound as ET antagonist.

Receptor binding assay using rat hippocampal membrane preparation

Rat hippocampi were obtained from freshly sacrificed male Sprague-Dawley rats and placed in ice cold 0.25M sucrose, 5 mM tris-HCl, pH 7.4 containing 0.5 μg/mL leupeptin, 7 μg/mL pepstatin A. Hippocampi were weighed and placed in a Dounce homogenizer with 25 volumes (wet weight to volume) ice-cold sucrose buffer in the presence of protease inhibitors. Hippocampi were homogenized using the Dounce (glass-glass) homogenizer with type A pestle, with the homogenizer immersed in ice. Tissue homogenate was centrifuged at 750×g for 10 min at 4° C. Supernatant was filtered through dampened cheesecloth, and centrifuged again at 48,000×g for 30 min at 4° C. Membrane pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}I$]-endothelin-1 (2000–2200 Ci/μmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}I$ radioactivity in a gamma counter. Nondisplaceable binding of [$^{125}I$]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration ($IC_{50}$) which gives 50% displacement of the total specifically bound [$^{125}I$]-endothelin-1 was presented as a measure of the potency of such compounds as endothelin antagonists.

Receptor binding assay using cloned human ET receptors expressed in Chinese Hamster Ovary Cells Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM $NaH_2PO_4$, 15 mM glucose, 10 mM tris/HEPES pH 7.4 Cells were centrifuged at 250×g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM [$^{125}I$]-endothelin-1 (2000–2200 Ci/μmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pad and washed with 150 mM NaCl, 0.1% BSA.

The filters were assayed for $^{125}I$ radioactivity in a gamma counter. Nondisplaceable binding of [$^{125}I$]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration ($IC_{50}$) which gives 50% displacement of the total specifically bound [$^{125}I$]-endothelin-1 was presented as a measure of the potency of such compounds as endothelin antagonists.

The binding assays described above were used to evaluate the potency of interaction of the compound of the invention with endothelin receptors. To determine whether this compound was an endothelin antagonist, assays which measure the ability of the compound to inhibit endothelin-stimulated phosphatidylinositol hydrolysis were established. Rat uterus contains predominantly one of the known endothelin receptor subtypes ($ET_A$).

Phosphatidylinositol hydrolysis assays using rat uterine slices

Diethylstilbestrol primed female Sprague-Dawley rats were sacrificed and their uteri were collected, dissected of fat and connective tissue and minced. Minced tissue was added to oxygenated (95% $O_2$, 5% $CO_2$) 127 mM NaCl, 25 mM $NaHCO_3$, 10 mM Glucose, 2.5 mM KCl, 1.2 mM $KH_2PO_4$, 1.2 nM $MgSO_4$, 1.8 mM $CaCl_2$. To the tissue mince, 1.2 μM myo-[$^3H$]-inositol (Amersham) was added. The mince was incubated 90 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to a final concentration of 3 nM to start the assay. Assays were done in quadruplicate. Samples were incubated at 37° C. under blowing $O_2$ in a hooded water bath for 30 minutes. Reaction was stopped by addition of trichloroacetic acid to 6% concentration. Samples were sonicated for 10 min. centrifuged 20 min, then trichloroacetic acid was extracted with water-saturated ethyl ether. An aliquot of each sample was neutrallized and diluted by addition of 50 mM tris-HCl pH 7.4. A 100 μL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal.

Inhibitory concentration (IC$_{50}$) is the concentration of test compound required to give a sample activity of 50% of control value.

Sarafotoxin S6c is a member of the endothelin family which binds preferentially to one of the known endothelin receptor subtypes (ET$_B$).

Phosphatidylinositol hydrolysis assays using rat lung slices

Male Sprague-Dawley rats were sacrificed and their lungs were collected, dissected of fat and connective tissue and minced. Minced tissue was added to oxygenated (95% O$_2$, 5% CO$_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 $\mu$M myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and sarafotoxin S6c (to a final concentration of 3 nM) with and without test compounds was added to start the assay. Assays were done in quadruplicate. Samples were incubated at 37° C. under blowing O$_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 nM tris-HCl pH 7.4. A 100 $\mu$L aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration (IC$_{50}$) is the concentration of test compound required to give a sample activity of 50% of control value.

Phosphatidylinositol hydrolysis assays using cloned human endothelin receptors expressed in Chinese Hamster Ovary cells Endothelin receptors of both receptor subtypes were cloned from a human cDNA library and were individually expressed in Chinese Hamster Ovary cells. Cells were loaded overnight by the addition of 1.2 $\mu$M myo-[$^3$H]-inositol to their growth medium. Cells were harvested by addition of 126 mM NaCl, 5 mM KCl, 2 mM EDTA, 1 mM NaH$_2$PO$_4$, 15 mM glucose, 10 mM tris-/HEPES pH 7.4 Cells were washed five times by centrifugation at 250×g for 5 minutes to remove excess radiolabelled inositol. The supernatant was aspirated off, and the cells were resuspended in the same oxygenated (95% O$_2$, 5% CO$_2$) buffer containing 10 mM LiCl, aliquotted into tubes, and endothelin-1 (to a final concentration of 0.3 nM) with and without test compounds was added to start the assay. Assays were done in quadruplicate. Samples were incubated at 37° C. under blowing O$_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 $\mu$L aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration (IC$_{50}$) is the concentration of test compound required to give a sample activity of 50% of control value.

Using the methodology described above, the compounds of the invention were evaluated and found to exhibit IC50 values of at least <50 $\mu$M thereby demonstrating and confirming the utility of the compound of this invention as an effective endothelin antagonist.

Accordingly the novel compounds of the present invention are useful in human therapy for treating asthma, hypertension, pulmonary hypertension, arterioscelerosis, heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, by administration to a patient in need of such treatment of a therapeutically effective amount thereof.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 mg.–1.0 g. per patient per day which can be administered in single or multiple doses. Preferably, the dosage range will be about 0.5–500 mg. per patient per day; more preferably about 0.5–100 mg. per patient per day.

The present invention also relates to pharmaceutical compositions for treating asthma, hypertension, pulmonary hypertension, arterioscelerosis, heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, comprising a therapeutically effective amount of the novel compound of this invention together with a pharmaceutically acceptable carrier therefor.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered as limiting the invention set forth in the claims appended hereto.

EXAMPLE 1

General procedure for the synthesis of 2-bromophenylacetic esters from substituted aromatic aldehydes Step A: Preparation of 2-trimethylsilyloxy-2-arylacetonitrile To a solution of 8.33 mmol of an appropriate aromatic aldehyde dissolved in 20 mL of dichloromethane is added 10.0 mmol of trimethylsilylcyanide, 1-2 mg of potassium cyanide, 1-2 mg of 18-crown-6, and the reaction mixture is stirred at room temperature for 3-12 hours. The reaction mixture is then diluted into diethyl ether, washed with 5% $NaHCO_3$, brine, dried ($MgSO_4$), filtered and evaporated. The residual oil is used directly in the next step.

Step B: Preparation of methyl 2-hydroxy-2-arylacetate

To a stirred 0° C. (ice-water bath) solution of 8.35 mmol of the product of Step A dissolved in 10 mL of methanol is introduced a slow stream of anhydrous hydrogen chloride gas. After 5 minutes the hydrogen chloride is turned off and the flask is stoppered and stirred at room temperature 14 hours. The reaction is then poured into ice-water and extracted into chloroform. The chloroform solution is filtered through a pad of silica gel and the silica gel is washed with additional chloroform. The combined filtrate is evaporated in vacuo to give the title compound.

Step C: Preparation of methyl 2-bromo-2-arylacetate

To a cooled (0° C.) solution of 2.19 mmol of the product of Step B dissolved in 10 mL of dichloromethane is added 2.74 mmol of triphenylphosphine followed by 2.74 mmol of carbon tetrabromide. After 30 minutes the reaction is allowed to warm to room temperature and stirring is continued for 2-12 hours. The reaction mixture is evaporated in vacuo, and the residue is purified on a silica gel flash chromatography column using an appropriate eluting solvent to afford the title compound.

EXAMPLE 2

General procedure for the alkylation of heterocycles with 2-bromophenylacetic esters Step A: Alkylation of the heterocycle A suspension of an appropriate heterocycle (5.71 mmol) and NaH (1.1 eq) in DMF (25 mL) is stirred for 1 hour and then cooled to 0° C. An appropriate 4-benzyloxybenzyl halide (1.1 eq) is then added and the ice bath removed. The reaction mixture is stirred for 2-4 hours and then concentrated in vacuo. The residue is purified on a silica gel flash chromatography column using an appropriate eluting solvent to yield the desired product.

Step B: Removal of the protecting group

To a solution of the product of Step A (1.62 mmol) in 10 mL of MeOH is added 60 mg of a 10% Pd/C catalyst and stirred under a $H_2$ atmosphere (1 atm) for 7 hours. The reaction mixture is filtered and concentrated in vacuo to yield the corresponding phenolic compound.

Step C: Alkylation of the phenolic component

To a suspension of 0.32 mmol of a 35% oil dispersion of potassium hydride in 0.5 mL of DMF is added 0.32 mmol of the phenolic compound (Step B) and the reaction is stirred under an $N_2$ atmosphere. After stirring for 15 minutes, a catalytic amount of 18-crown-6 is added followed by addition of a solution of 0.35 mmol of the product of Example 1 (Step C) dissolved in 1.0 mL of DMF. The reaction mixture, after stirring for 4 hours, is concentrated in vacuo, and the residue is purified on a silica gel flash chromatography column using an appropriate solvent system to afford the title compound.

Step D: General procedure for ester hydrolysis

To a solution of 0.21 mmol of the product of Step C dissolved in 3 mL of ethanol is added 1 mL of a 1N NaOH solution. The reaction mixture is stirred at room temperature for 1.5 hours, neutralized to pH 7 with 1N HCl and then concentrated in vacuo. The residue is purified on a silica gel flash chromatography column to afford the corresponding carboxylic acid.

EXAMPLE 3

Alkyl 2-[(4-bromomethyl-2,6-dipropyl)phenoxy]2-arylacetic acids (A general procedure)

Step A: Preparation of alkyl 2-bromo-2-arylacetate

Method A: (from phenylacetic acids)

A substituted phenylacetic acid is converted to the corresponding methyl ester by refluxing the acid in methanol in the presence of a catalytic amount of conc.

sulfuric acid. The ester, thus obtained, is then refluxed in carbon tetrachloride with N-bromosuccinimide (1.1 equiv) and AIBN (0.05–0.1 equiv). Upon completion of the reaction, the product methyl 2-bromo-2-phenylacetate is purified by flash column chromatography using silica gel and ethyl acetate in hexane as eluent.

Method B: (from aromatic aldehydes)

An appropriately substituted aromatic aldehyde is treated overnight with trimethylsilyl cyanide in the presence of catalytic amounts of KCN and 18-crown-6 in methylene chloride. The reaction mixture is quenched with water and extracted with $CH_2Cl_2$/ethyl acetate/ether (1/2/2) mixture. The organic phase is washed with saturated aq. $NaHCO_3$ solution. After drying and concentration of the organic phase, the trimethylsilyl cyanohydrin obtained is used in the next acid hydrolysis step. Gaseous HCl is bubbled through an ethanolic solution of the cyanohydrin at 0° C. for 0.5 h, and the resulting mixture is stirred overnight or for a longer period of time to afford the corresponding crude 2-hydroxy ester. The ester is then treated with triphenylphosphine and carbon tetrabromide in methylene chloride at 0° C. Methylene chloride is removed and flash column chromatography of the crude product using silica gel and ethyl acetate/hexane as eluent gives the desired 2-bromo-2-arylacetate derivative.

Step B: Alkylation of the phenol 4-hydroxy-3,5-dipropylbenzyl alcohol is alkylated with 2-bromo-2-aryl esters (Step A) in DMF using either cesium carbonate ($Cs_2CO_3$), or potassium carbonate ($K_2CO_3$), or sodium hydride (NaH) at room temperature. The alkylated product is purified by flash column chromatography using silica gel and ethyl acetate/hexane mixture as eluent to give the desired 4-[(1-carbomethoxy-1-aryl)methoxy]-3,5-dipropyl-benzyl alcohol.

Step C: Preparation of 4-[(1-carbomethoxy-1-aryl)methoxy]-3,5-dipropylbenzyl bromide The product (1.39 mmol) obtained in Step B is reacted with $CBr_4$ (2.1 mmol) and $Ph_3P$ (2.1 mmol) in dry THF (10 mL) containing dry acetonitrile (5 mL) at room temperature for 3–6 h. The solvent is removed and the crude product is purified by flash column chromatography (silica gel) using an appropriate mixture of ethylacetate and hexane to give the titled product as an oil.

EXAMPLE 4

3-[4-((1-Carboxy-1-(2-methoxyphenyl))methoxy)-phenylmethyl]-7-methyl-2-propyl-3H-imidazo[4,5-b]pyridine Step A: Preparation of ethyl 2-bromo-2-(2-methoxyphenyl)acetate Using the general procedure for the synthesis of 2-bromophenylacetic esters from benzaldehydes (Steps A–C, Example 1), 1.00 g (7.35 mmol) of 2-methoxybenzaldehyde was converted to 0.736 g (2.69 mmol) of the title compound in 37% overall yield.

$^1$H NMR (300 MHz, $CDCl_3$, ppm): δ 1.20–1.30 (t, 3H), 3.85 (s, 3H), 4.15–4.30 (m, 2H), 5.85 (s, 1H), 6.80–6.90 (d, 1H), 6.90–7.00 (t, 1H), 7.25–7.35 (t, 1H), 7.55–7.65 (d, 1H).

Step B: Preparation of 3-[4-((1-carbomethoxy-1-(2-methoxyphenyl))methoxy)phenylmethyl]-7-methyl-2-propyl-3H-imidazo[4,5-b]pyridine Using the general procedure for the alkylation reaction described in Step C of Example 2, 0.090 g (0.32 mmol) of 3-(4-hydroxyphenyl)methyl-7-methyl-2-propyl-3H-imidazo[4,5-b]pyridine (prepared according to Step A–B of Example 2) was alkylated with 0.096 g (0.35 mmol) of the product of Step A, to afford 0.126 g (83%) of the title compound.

$^1$H NMR (300 MHz, $CDCl_3$, ppm): δ 0.90–1.00 (t, 3H), 1.15–1.25 (m, 3H), 1.65–1.80 (m, 2H), 2.65 (s, 3H), 2.70–2.80 (t, 2H), 4.05–4.25 (m, 2H), 5.35 (s, 2H), 6.05 (s, 1H), 6.80–7.05 (m, 7H), 7.25–7.35 (m, 1H), 7.45–7.50 (d, 1H), 8.15–8.20 (d, 1H).

FAB-MS: m/e 474 (M+1).

Step C: Preparation of 3-[4-((1-carboxy-1-(2-methoxyphenyl))methoxy)phenyl)methyl[-7-methyl-2-propyl-3H-imidazo[4,5-b]pyridine Using the general procedure for ester hydrolysis described in Step D of Example 2, 0.123 g (0.26 mmol) of the product of Step B was converted to 0.095 g (82%) of the title compound.

$^1$H NMR (300 MHz, $CD_3OD$, ppm): δ 0.90–1.00 (t, 3H), 1.60–1.80 (m, 2H), 2.60 (s, 3H), 2.80–2.90 (t, 2H), 3.90 (s, 3H), 5.50 (s, 2H), 6.00 (s, 1H), 5.90–7.15 (m, 6H), 7.15–7.20 (d, 1H), 7.20–7.25 (t, 1H), 7.45–7.55 (d, 1H), 8.20–8.25 (d, 1H).

FAB -MS: m/e 446 (M+1).

EXAMPLE 5

3-[4-((1-Carboxy-1-(2-methoxyphenyl))methoxy)-3-propylphenylmethyl]-5,7-dimethyl-2-ethyl-3H-imidazo[4,5-b]pyridine Step A: Preparation of 3-[4-((1-carbomethoxy-1-(2-methoxyphenyl))-methoxy)-3-propylphenylmethyl]-5,7-dimethyl-2-ethyl-3H-imidazo-[4,5-b]pyridine Using the $K_2CO_3$/acetone conditions for phenol alkylation described in Step B of Example 3,5,7-dimethyl-2-ethyl-3-[4-hydroxy-3-propylphenyl]methyl-3H-imidazo[4,5-b]pyridine (prepared as described in the patent application WO 91/11999) was alkylated with methyl 2-bromo-2-(2-methoxy)acetate. Standard workup and purification by flash chromatography afforded a 69% yield of the title compound.

$^1$H NMR (400 MHz, $CDCl_3$, ppm): δ 7.6 (d, 1H), 7.38 (dd, 1H), 6.98 (dd, 1H), 6.875 (s, 1H), 6.866 (dd, 1H), 6.8–6.75 (m, 2H), 6.62 (d, 1H), 5.975 (s, 1H), 5.35 (ABq, 2H), 3.85 (s, 3H), 3.68 (s, 3H), 2.79 (q, 2H), 2.62 (s, 3H), 2.575 (s, 3H), 2.466 (dd, 1H), 1.65–1.47 (m, 2H), 1.27 (t, 3H), 0.9 (t, 3H).

FAB-MS: m/e 502 (M+1).

Step B: Preparation of 3-[4-((1-carboxy-1-(2-methoxyphenyl))methoxy)-3-propylphenylmethyl]-5,7-dimethyl-2-ethyl-3H-imidazo[4,5-b]pyridine Using the general procedure for ester hydrolysis described in Step D of Example 2, the product of Step A was converted to the title compound in 58% yield.

$^1$H NMR (400 MHz, $CDCl_3$, ppm): δ 7.8 (d, 1H), 7.4 (dd, 1H), 7.16 (d, 1H), 6.99 (d, 1H), 6.875 (s, 1H), 6.825 (d, 1H), 6.775 (d, 1H), 6.72 (d, 1H), 6.02 (br s, 1H), 5.33 (ABq, 2H), 3.83 (s, 3H), 2.72 (q, 2H), 2.575 (s, 3H), 2.49 (s, 3H), 1.7–1.47 (m, 2H), 0.97 (t, 3H), 0.9 (t, 3H).

FAB-MS: m/e 488 (M+1).

EXAMPLE 6

3-[4-((1-Carboxy-1-(2,5-dibromo-3,4-dimethoxyphenyl))methoxy)-3-propylphenylmethyl]-5,7-dimethyl-2-ethyl-3H-imidazo[4,5-b]pyridine Step A: Preparation of methyl 2,2′,5′-tribromo-3,4-dimethoxyphenyl-acetate A mixture of 5.0 g (25 mmol) of 3′,4′-dimethoxyphenylacetic acid and thionyl chloride 2.32 mL (1.25 eq.) was stirred and refluxed while bromine 4.5 mL, 3.5 eq.) was added dropwise to the reaction mixture. The reaction was refluxed overnight then cooled. Methanol (30 mL) was cautiously added and the reaction mixture was stirred an additional 1 hour at room temperature. The mixture was then evaporated in vacuo, and the residue was purified on a silica gel flash chromatography column eluted with 10% ethyl acetate/hexane to afford 0.80 g (7%) of the title compound.

$^1$H NMR (400 MHz, CDCl$_3$, ppm): δ 7.37 (s, 1H), 5.94 (s, 2H), 3.88 (s, 3H), 3.85 (s, 3H), 3.79 (s, 3H).

FAB-MS: m/e 445 (M+1).

Step B: Preparation of 3-[4-((1-carbomethoxy-1-(2,5-dibromo-3,4-dimethoxyphenyl))methoxy)-3-propylphenylmethyl]-5,7-dimethyl -2-ethyl-3H-imidazo[4,5-b]pyridine Using the K$_2$CO$_3$/acetone conditions for phenol alkylation described in Step B of Example 3, 5,7-dimethyl-2-ethyl-3-[4-hydroxy -3-propylphenyl]methyl-3H-imidazo[4,5-b]pyridine was alkylated with the product of Step A. Standard workup and purification by flash chromatography afforded a 65% yield of the title compound.

$^1$H NMR (400 MHz, CDCl$_3$, ppm): δ 7.15 (s, 1H), 6.98 (dd, 1H), 6.86 (s, 1H), 6.79 (dd, 1H), 6.54 (d, 1H, 8.42 Hz), 6.04 (s, 1H), 5.22 (ABq, 2H), 3.825 (s, 3H), 3.8 (s, 3H), 3.713 (s, 3H), 2.76 (q, 2H, 7.6 Hz), 2.59 (s, 3H), 2.561 (s, 3H), 2.477 (dd, 2H, 7.65 Hz, 7.6 Hz), 1.675–1.45 (m, 2H), 1.268 (t, 3H), 0.889 (t, 3H).

FAB-MS: m/e 688, 690, 692 (M+1).

Step C: Preparation of 3-[4-((1-carboxy-1-(2,5-dibromo-3,4-dimethoxyphenyl))methoxy)-3-propylphenylmethyl]-5,7-dimethyl-2-ethyl-3H-imidazo[4,5-b]pyridine Using the general procedure for ester hydrolysis described in Step D of Example 2, the product of Step B was convened to the title compound in 72% yield.

$^1$H NMR (400 MHz, CDCl$_3$, ppm): δ 7.25 (br s, 1H), 6.97 (s, 1H), 6.94 (s, 1H), 6.82 (br s, 1H), 6.68 (br s, 1H), 5.41 (s, 3H), 3.80 (s, 3H), 3.78 (s, 3H), 2.80 (m, 2H), 2.58 (s, 3H), 2.56 (s, 3H), 2.22 (m, 2H), 1.8–1.45 (m, 2H), 1.25 (t, 3H), 0.84 (t, 3H).

FAB-MS: m/e 675 (M+1).

EXAMPLE 7

3-[4-((1-Carboxy-1-(3,4-dimethoxyphenyl))methoxy)-3-propylphenylmethyl]-5,7-dimethyl-2-ethyl-3H-imidazo[4,5-b]pyridine Step A: Preparation of 3-[4-((1-carbomethoxy-1-(3,4-dimethoxyphenyl))methoxy)-3-propylphenylmethyl]-5,7-dimethyl-2-ethyl-3H-imidazo[4,5-b]pyridine To a solution of 63 mg (0.09 mmol) of the product of Step B of Example 6 in methanol was added 5 mg of palladium chloride, 20 mg of sodium borohydride and the mixture was stirred at room temperature for 2 hours. The reaction mixture was evaporated in vacuo, and the residue was purified on a silica gel flash chromatography column eluted with 50% ethyl acetate/hexane to afford 22 mg (45%) of the title compound.

$^1$H NMR (400 MHz, CDCl$_3$, ppm): δ 7.07 (s, 1H), 7.04 (d, 1H, 8.13 Hz), 6.97 (s, 1H), 6.85 (s, 1H), 6.85 (d, 1H), 6.78 (dd, 1H), 6.57 (d, 1H), 5.48 (s, 1H), 5.33 (s, 1H), 3.86 (s, 3H), 3.85 (s, 3H), 3.65 (s, 3H), 2.75 (q, 2H, 7.52 Hz), 2.59 (s, 3H), 2.56 (s, 3H), 2.65-2.5 (m, 2H), 1.72–1.47 (m, 2H), 1.252 (t, 3H, 7.69 Hz), 0.89 (t, 3H, 7.34 Hz).

FAB-MS: m/e 532 (M+1)

Step B: Preparation of 3-[4-((1-carboxy-1-(3,4-dimethoxyphenyl))methoxy)-3-propylphenylmethyl]-5,7-dimethyl-2-ethyl-3H-imidazo[4,5-b]pyridine Using the general procedure for ester hydrolysis described in Step D of Example 2, the product of Step A was converted to the title compound in 90% yield.

$^1$H NMR (400 MHz, CDCl$_3$, ppm): δ 7.2 (s, 1H), 7.14 (d, 1H), 6.98 (s, 1H), 6.84 (d, 1H), 6.82 (s, 1H), 6.74 (d, 1H), 6.65 (d, 1H), 5.5 (s, 1H), 5.3 (ABq, 2H), 3.86 (s, 3H), 3.84 (s, 3H), 2.62 (q, 2H), 2.7–2.55 (m, 2H), 2.52 (s, 3H), 2.39 (s, 3H), 1.7–1.47 (m, 2H), 1.22 (t, 3H), 0.89 (t, 3H).

FAB-MS: m/e 518 (M+1).

EXAMPLE 8

3-[4-((1-carboxy-1-phenyl)methoxy)-3,5-dipropylphenyl]methyl-5,7-dimethyl-2-ethyl-3H-imidazo[4,5-b]pyridine Step A: Preparation of methyl 3-(2propen-1-yl)-4-(2-propen-1-yl-oxy)benzoate A solution of 3.04 g (15.8 mmol) of methyl 4-hydroxy-3-propenylbenzoate (prepared by the procedure described in patent application WO91/11999) was refluxed with anhydrous potassium carbonate (4.37 g, 2 equiv) and allyl bromide (3.5 mL, 2.5 equiv) in acetone overnight. The mixture was filtered through celite and the filter cake was washed with acetone and dichloromethane. After removing the solvents, the resulting oil was distilled under high vacuum to give 3.2 g (87%) of the title compound.

$^1$H NMR (400 MHz, CDCl$_3$, ppm): δ 7.87 (dd, 1H), 7.83 (d, 1H), 6.83 (d, 1H), 6.07–5.92 (m, 2H), 5.41 (dd, 1H), 5.27 (dd, 1H), 5.07 (dd, 1H), 5.05 (dd, 1H), 4.58 (d, 2H), 3.83 (s, 3H), 3.4 (d, 2H).

Step B: Preparation of methyl 4-hydroxy-3,5-di(2-propen-1-yl)benzoate

The product of Step A (3.2 g, 13.8 mmol) was refluxed in 1,2-dichlorobenzene for 3 days in the presence of a catalytic amount of BHT (10 mg). Flash column chromatography of the mixture using hexane and then 10% and 20% ethyl acetate in hexane afforded 3.1 g (97%) of the title compound.

$^1$H NMR (200 MHz, CDCl$_3$, ppm): δ 7.73 (s, 2H), 6.12–5.92 (m, 2H), 5.63 (s, 1H), 5.21 (dd, 2H), 5.15 (dd, 2H), 3.87 (s, 3H), 3.43 (dd, 4H).

FAB-MS: m/e 232 (M+1).

Step C: Preparation of methyl 4-tert-butyldimethylsilyloxy-3,5-di(2-propen-1-yl)benzoate The product of Step B (3.1 g, 13.36 mmol) was treated with tert-butyldimethylsilyl chloride (2.22 g, 1.1 equiv), triethylamine (3 mL) and DMAP (0.1 equiv) in dichloromethane overnight. The mixture was concentrated and flash chromatographed with 5% and then 10% ethyl acetate in hexane to finish 4.5 g (97%) of the title compound.

$^1$H NMR (200 MHz, CDCl$_3$, ppm): δ 7.72 (s, 2H), 6.02–5.30 (m, 2H), 5.12 (dd, 2H), 5.07 (dd, 2H), 3.86 (s, 3H), 3.38 (dd, 4H, 7 Hz), 1.02 (s, 9H), 0.21 (s, 6H).

Step D: Preparation of methyl 4-tert-butyldimethylsilyloxy-3,5-dipropylbenzoate

A solution of 5.0 g (14.45 mmol) of the product of Step C in 250 mL ethanol containing 5% Rh/C (0.25 g) was shaken under a 40 psi pressure of hydrogen. Upon completion of reduction, the mixture was filtered through celite, the filter cake was washed with methanol and dichloromethane. Removal of solvents afforded 4.55 g (90%) of the title compound.

¹H NMR (200 MHz, CDCl₃, ppm): δ 7.66 (s, 2H), 3.84 (s, 3H), 2.54 (dd, 4H, 7.91 Hz, 7.41 Hz), 1.56 (sextet, 4H), 0.98 (s, 9H), 0.899 (t, 6H), 0.18 (s, 6H).

Step E: Preparation of 4-tert-butyldimethylsilyloxy-3,5-dipropylbenzyl alcohol

Lithium aluminum hydride (9 mL of a 1M solution in THF) was added cautiously to a solution of the product of Step D at 0° C., and the reaction mixture was stirred overnight. Ethyl acetate was added to the mixture, cooled to 0° C. and treated with cold 1N HCl. After separating the organic phase, the aqueous phase was extracted with a mixture of ethyl acetate-ether-dichloromethane. The combined organic extracts were dried and concentrated. The concentrated material was purified by flash column chromatography using 20% ethyl acetate in hexane to afford 4.2 g (92%) of the title compound.

¹H NMR (400 MHz, CDCl₃, ppm): δ 6.95 (s, 2H), 4.54 (s, 2H), 2.52 (dd, 4H), 1.55 (sextet, 4H), 0.99 (s, 9H), 0.90 (t, 6H), 0.16 (s, 6H).

Step F: Preparation of 3-[4-tert-butyldimethylsilyloxy-3,5-dipropylphenylmethyl]-5,7-dimethyl-2-ethyl-3H-imidazo -[4,5-b]-pyridine To a solution of 4.2 g ( 13.0 mmol) of the product of Step E, 2.5 g (14.0 mmol) of 5,7-dimethyl-2-ethylimidazo[4,5-b]pyridine (prepared by the method described in patent application WO 91/11999), and 5.62 (20.0 mmol) of triphenylphosphine dissolved in 40 mL of THF, was added 3.396 g (20.0 mmol) of diethyl azodicarboxylate and the mixture was stirred for 1 hour. The reaction mixture was then concentrated in vacuo and the residual oil was purified on a silica gel flash chromatography column eluted with 25–40% ethyl acetate/hexane to afford 5 g (80%) of the title compound.

¹H NMR (400 MHz, CDCl₃, ppm): δ 6.84 (s, 1H), 6.71 (s, 2H), 5.29 (s, 2H), 2.75 (q, 2H), 2.57 (s, 3H), 2.55 (s, 3H), 2.4 (dd, 4H), 1.42 (sextet, 4H), 1.27 (t, 3H), 0.94 (s, 9H), 0.8 (t, 6H), 0.10 (s, 6H).

Step G: Preparation of 5,7-dimethyl-2-ethyl-3-[(4-hydroxy-3,5-dipropylphenyl)methyl]-3H-imidazo[4,5-b]pyridine A THF solution of 5.0 g (10.44 mmol) of the product of Step F was treated with tetrabutylammonium fluoride (1.2 equiv, 1M solution in THF) overnight. THF was removed in vacuo and the residue was flash chromatographed using 30–50% ethyl acetate in hexane as eluent to afford 3.35 g (88%) of the title compound.

¹H NMR (400 MHz, CDCl₃, ppm): δ 6.86 (s, 1H), 6.81 (s, 1H), 6.73 (s, 2H), 5.37 (s, 1H), 5.30 (s, 2H), 2.76 (q, 2H), 2.6 (s, 3H), 2.56 (s, 3H), 2.44 (dd, 4H), 1.52 (sextet, 4H), 1.23 (t, 3H), 0.88 (t, 6H).

Step H: Preparation of 3-[4-((1-carbomethoxy-1-phenyl)methoxy)-3,5-dipropylphenylmethyl]-5,7-dimethyl-2-ethyl-3H-imidazo-[4,5-b]pyridine Using the K₂CO₃/acetone conditions for phenol alkylation described in Step B of Example 3, the product of Step G was alkylated with methyl 2-bromophenylacetate. Standard workup and purification by flash chromatography afforded a 96% yield of the title compound.

¹H NMR (400 MHz, CDCl₃, ppm): δ 7.44–7.42 (m, 2H), 7.37–7.31 (m, 3H), 6.88 (s, 1H), 6.74 (s, 2H), 5.38 (s, 1H), 5.33 (s, 2H), 3.7 (s, 3H), 2.80 (q, 2H), 2.62 (s, 3H), 2.57 (s, 3H), 2.38 (dd, 2H), 2.3–2.25 (m, 2H), 1.55–1.47 (m, 2H), 1.46–1.37 (m, 2H), 1.36 (t, 3H), 0.86 (t, 3H), 0.72 (t, 3H).

FAB-MS: m/e 514 (M+1).

Step I: Preparation of 3-[4-((1-carboxy-1-phenyl)methoxy)-3,5-dipropylphenyl]methyl-5,7-dimethyl-2-ethyl-3H-imidazo-[4,5-b]pyridine Using the general procedure for ester hydrolysis described in Step D of Example 2, the product of Step H was converted to the title compound in 80% yield.

¹H NMR (400 MHz, CDCl₃, ppm): δ 7.47–7.34 (m, 2H), 7.33–7.22 (m, 3H), 6.92 (s, 1H), 6.69 (s, 2H), 5.35 (br s, 3H), 2.78 (q, 2H), 2.58 (s, 3H), 2.55 (s, 3H), 2.62–2.25 (m, 4H), 1.45–1.28 (m, 4H), 1.2 (t, 3H), 0.7 (t, 6H).

FAB-MS: m/e 500 (M+1).

EXAMPLE 9

3-[4-((1-Carboxy-1-(2-methoxyphenyl))methoxy)-3,5-dipropylphenylmethyl]-5,7-dimethyl-2-ethyl-3H-imidazo[4,5-b]pyridine Step A: Preparation of 3-[4-((1-carbomethoxy-1-(2-methoxyphenyl))-methoxy)-3,5-dipropylphenyl]methyl-5,7 -dimethyl-2-ethyl-3H -imidazo[4,5-b]pyridine Using the K₂CO₃/acetone conditions for phenol alkylation described in Step B of Example 3,5,7-dimethyl-2-ethyl-3-[4-hydroxy-3,5-dipropylphenyl]methyl-3H-imidazo[4,5-b]pyridine was alkylated with methyl 2-bromo-(2'-methoxy)phenylacetate. Standard workup and purification by flash chromatography afforded the title compound.

¹H NMR (400 MHz, CDCl₃, ppm): δ 7.62 (dd, 1H, J=2.1, 1.9 Hz), 7.40 (dd, 1H), 7.30 (dd, 1H), 6.86 (s, 1H), 6.72 (s, 2H), 6.70 (dd, 1H), 5.37 (s), 5.35 (s), 5.32 (s, 2H), 3.69 (s, 3H), 3.68 (s, 3H), 2.74 (q, 2H, J=7.5 Hz), 2.61 (s, 3H), 2.56 (s, 3H), 2.34–2.19 (m, 4H), 1.50–1.29 (m, 4H), 1.23 (t, 3H, J=7.54 Hz), 0.74 (t, 6H, J=7.3 Hz).

FAB-MS: m/e 544 (M+1).

Step B: Preparation of 3-[4-((1-carboxy-1-(2-methoxyphenyl))methoxy)-3,5-dipropylphenylmethyl]-5,7-dimethyl-2-ethyl-3H-imidazo[4,5-b]-pyridine Using the general procedure for ester hydrolysis described in Step D of Example 2, the product of Step A was converted to the title compound in 77% yield.

¹H NMR (400 MHz, CDCl₃, ppm): δ 7.72–7.66 (m), 7.55 (br s, 1H), 7.52–7.48 (m), 7.35 (dd, 1H), 6.86 (s, 1H), 6.72 (s, 2H), 6.69 (dd, 1H), 5.38 (s, 1H), 5.30 (ABq, 2H), 3.64 (s, 3H), 2.76 (q, 2H, 7.6 Hz), 2.55 (s, 3H), 2.52 (s, 3H), 2.28 (m, 4H), 1.50–1.18 (m, 4H), 1.13 (t, 3H), 0.74 (t, 6H).

FAB-MS: m/e 608 (M+2K).

EXAMPLE 10

3-[4-(1-Carboxy-1-(3-methoxyphenyl)methoxy)-3,5-dipropylphenylmethyl]-5,7-dimethyl-2-ethyl-3H-imidazo-[4,5-b]pyridine The title compound was prepared according to the synthetic route described for Example 8 except for Step H where methyl 2-bromo-(3'-methoxy)phenylacetate was used as the alkylating agent.

¹H NMR (200 MHz, CD₃OD, ppm): δ 7.26 (t, 1H, J=7.8 Hz), 7.02–6.90 (m, 4H), 6.77 (s, 2H), 5.44 (s, 1H), 5.00 (s, 1H), 3.77 (s, 3H), 2.84 (q, 2H, J=7.6 Hz), 2.60 (s, 3H), 2.58 (s, 3H), 2.31 (t, 4H, J=7.8 Hz), 1.45–1.29 (m, 4H), 1.21 (t, 3H, J=7.6 Hz), 0.74 (t, 6H, J=7.3 Hz).

FAB-MS m/e=530 (M+1).

EXAMPLE 11

3-[4-(1-Carboxy-1-(4-methoxyphenyl)methoxy)-3,5-dipropylphenylmethyl]-5,7-dimethyl-2-ethyl-3H-imidazo[4,5-b]pyridine The title compound was prepared according to the synthetic route described for Example 8 except for Step H where methyl 2-bromo-(4'-methoxy)phenylacetate was used as the alkylating agent.

$^1$H NMR (200 MHz, CD$_3$OD, ppm): δ 7.27 (d, 2H, J=8.8 Hz), 7.19 (s, 1H), 6.92–6.89 (m, 4H), 5.53 (s, 2H), 5.00 (s, 1H), 2.97 (q, 2H, J=7.5 Hz), 2.62 (s, 6H), 2.31 (t, 4H, J=7.8 Hz), 1.46–1.17 (m, 4H), 1.25 (t, 3H, J=7.6 Hz), 0.75 (t, 6H, J=7.3 Hz).

FAB-MS m/e=530 (M+1).

EXAMPLE 12

3-[4-((1-Carboxy-1-(2,5-dibromo-3,4-dimethoxyphenyl))-methoxy)-3,5-dipropylphenylmethyl]-5,7-dimethyl-2-ethyl-3H-imidazo[4,5-b]-pyridine Step A: Preparation of 3-[4-((1-carbomethoxy-1-(2,5-dibromo-3,4-dimethoxyphenyl))methoxy)-3,5-dipropylphenylmethyl]-5,7-dimethyl-2-ethyl-3H-imidazo[4,5-b]pyridine Using the K$_2$CO$_3$/acetone conditions for phenol alkylation described in Step B of Example 3, the 5,7-dimethyl-2-ethyl-3-[4-hydroxy-3,5-dipropylphenyl]-methyl-3H-imidazo[4,5-b]pyridine was alkylated with methyl 2,2',5'-tribromo-3',4'-dimethoxyphenylacetate. Standard workup and purification by flash chromatography afforded a 60% yield of the title compound.

$^1$H NMR (400 MHz, CDCl$_3$, ppm): δ 7.36 (s, 1H), 6.89 (s, 1H), 6.75 (s, 2H), 5.55 (s, 1H), 5.34 (ABq, 2H), 3.88 (s, 3H), 3.84 (s, 3H), 3.69 (s, 3H), 2.78 (q, 2H), 2.62 (s, 3H), 2.41–2.20 (m, 4H), 1.45–1.32 (m, 4H), 0.85 (t, 3H), 0.74 (t, 6H).

FAB-MS m/e 732 (M+1).

Step B: Preparation of 3-[4-((1-carboxy-1-(2,5-dibromo-3,4-dimethoxyphenyl))-methoxy)-3,5-dipropylphenylmethyl]-5,7-dimethyl-2-ethyl-3H-imidazo[4,5-b]-pyridine Using the general procedure for ester hydrolysis described in Step D of Example 2, the product of Step A was convened to the title compound.

$^1$H NMR (400 MHz, CD$_3$OD, ppm): δ 7.45 (br s, 1H), 7.01 (s, 1H), 6.75 (s, 2H), 5.51 (s, 1H), 5.44 (ABq, 2H), 3.88 (s, 3H), 3.78 (s, 3H), 3.34 (s, 3H), 2.82 (q, J=7.5 Hz, 2H), 2.59 (s, 3H), 2.57 (s, 3H), 2.24–240 (m, 4H), 1.38–1.52 (m, 2H), 1.24–1.36 (m, 2H), 1.20 (t, J=7.5 Hz, 3H), 0.74 (t, J=7.5 Hz, 6H).

FAB-MS m/e 716 (M+1).

EXAMPLE 13

3-[4-(1-Carboxy-1-(3,4-methylenedioxyphenyl)methoxy)-3,5-dipropylphenylmethyl]-5,7-dimethyl-2-ethyl-3H-imidazo[4,5-b]pyridine The titled compound was prepared following the synthetic route described for the synthesis of Example 8 except for Step H where methyl 2-bromo-(3,4-methylenedioxyphenyl)acetate was used as the alkylating agent.

$^1$H NMR (400 MHz, CD$_3$OD): δ 7.15 (s, 1H); 6.95 (d, 1H, J=1.6 Hz), 6.86 (s, 2H); 6.83 (dd, 1H, J=8.0, 1.6 Hz), 6.77 (d, 1H, J=7.9 Hz), 5.96 (s, 2H), 5.51 (s, 2H), 4.96 (s, 1H), 2.96 (q, 2H, J=7.6 Hz), 2.62 (s, 3H), 2.61 (s, 3H), 2.32 (t, 4H, J=7.9 Hz), 1.43 (sx, 2H, J=7.6 Hz), 1.34 (sx, 2H, J=7.5 Hz), 1.24 (t, 2H, J=7.6 Hz), 0.77 (t, 6H, J=7.3 Hz).

FAB-MS m/e=544 (M+1)

EXAMPLE 14

3-[4-(1-Carboxy-1-(benzofur-5-yl)methoxy)-3,5-dipropylphenylmethyl]-5,7-dimethyl-2-ethyl-3H-imidazo-[4,5-b]pyridine The titled compound was prepared following the synthetic route described for the synthesis of Example 8 except for Step H where methyl 2-bromo-2-(benzofur-5-yl)acetate was used as the alkylating agent.

$^1$H NMR (400 MHz, CD$_3$OD): δ 7.78 (d, 1H, J=2.2 Hz), 7.66 (d, 1H, J=1.6 Hz), 7.49 (d, 1H, J=8.4 Hz), 7.40 (dd, 1H, J=1.8, 8.6 Hz), 7.03 (s, 1H), 6.82 (s, 1H), 6.76 (s, 2H), 5.44 (s, 2H), 5.13 (s, 1H), 2.84 (q, 2H, J=7.6 Hz), 2.60 (s, 3H), 2.57 (s, 3H), 2.27 (t, 4H, J=8.0 Hz), 1.34 (m, 4H), 1.20 (t, 3H, J=7.6 Hz), 0.68 (t, 6H, J=7.3 Hz).

EXAMPLE 15

3-[4-(1-Carboxy-1-(3,4-dimethoxyphenyl)methoxy)-3,5-dipropylphenylmethyl]-5,7-dimethyl-2-ethyl-3H-imidazo[4,5-b]pyridine The titled compound was prepared following the synthetic route described for the synthesis of Example 8 except for Step H where methyl 2-bromo-(3,4-dimethoxyphenyl)acetate was used as the alkylating agent.

$^1$H NMR (400 MHz, CD$_3$OD/CDCl$_3$, ppm): δ 7.06 (s, 1H), 6.98 (s, 1H), 6.85 (m, 2H), 6.73 (s, 1H), 5.437 (s, 1H), 5.41 (s, 2H), 3.81 (s, 3H), 3.782 (s, 3H), 2.83 (q, 2H), 2.59 (s, 3H), 2.56 (s, 3H), 2.27 (t, 4H), 1.45–1.38 (m, 2H), 1.31–1.15 (m, 2H), 1.207 (t, 3H), 0.73 (t, 3H).

EXAMPLE 16

3-[4-{1-Carboxy-1-(3,5-dimethoxyphenyl)methoxy}-3,5-dipropylphenylmethyl]-5,7-dimethyl-2-ethyl-3H-imidazo[4,5-b]pyridine The titled compound was prepared following the synthetic route described for the synthesis of Example 8 except for Step H where methyl 2-bromo-(3,5-dimethoxyphenyl)acetate was used as the alkylating agent.

$^1$H NMR (400 MHz, CD$_3$OD/CDCl$_3$, ppm) δ 6.96 (s, 1H), 6.72 (s, 2H), 6.57 (d, 2H), 6.39 (dt, 1H), 5.41 (s, 1H), 5.39 (s, 2H), 3.71 (s, 6H), 2.81 (q, 2H), 2.59 (s, 3H), 2.56 (s, 3H), 2.29 (t, 4H), 1.417 (m, 2H), 1.30 (M, 2H), 1.21 (t, 3H), 0.73 (t, 6H).

EXAMPLE 17

3-[4-(1-Carboxy-1-(indol-5-yl)methoxy)-3,5-dipropylphenylmethyl]-5,7-dimethyl-2-ethyl-3H-imidazo4,5-b]pyridine The titled compound was prepared following the synthetic route described for the synthesis of Example 8 except for Step H where methyl 2-bromo-2-(indol-5-yl)acetate was used as the alkylating agent.

$^1$H NMR (400 MHz, CD$_3$OD/CDCl$_3$, ppm): δ 7.46 (s, 1H), 7.22 (dd, 1H), 7.17 (d, 1H, J=3.09 Hz), 6.99 (s, 1H), 6.68 (s, 2H), 6.33 (d, 1H, J=3.23 Hz), 5.41 (ABq, 2H), 4.9 (s, 1H), 2.81 (q, 2H), 2.59 (s, 3H), 2.56 (s, 3H), 2.24–2.80 (m, 4H), 1.43–1.3 (m, 2H), 1.18 (t, 3H), 1.23–1.12 (m, 2H), 0.64 (t, 6H).

EXAMPLE 18

3-[4-(1-Carboxy-1-(3,4-methylenedioxyphenyl)-methoxy)-3,5-dipropylphenylmethyl]-2-methyl-3H-imidazo[4,5-b]pyridine Step A: Preparation of methyl 2-bromo-2-(3,4-methylenedioxyphenyl) acetate A mixture of (3,4-methylenedioxyphenyl)acetic acid (4.64 g, 25.74 mMol) in dry DMF (40 mL), cesium carbonate (9.2 g, 25.74 mMol) and methyl iodide (3.7 g, 26.0 mMol) in dry DMF (40 mL) was stirred at room temperature for 3 h. At the end of this period, the reaction mixture was poured into ice water and extracted with ethyl acetate. The organic phase was washed with saturated NaHCO₃, water, brine and then dried (MgSO₄) and filtered. The filtrate was concentrated in vacuo to provide pure methyl (3,4-methylenedioxyphenyl)acetate as an oil (4.38 g).

N-Bromosuccinimide (3.95 g, 22.2 mMol) and AIBN (0.098 g, 0.06 mMol) were added to a solution of methyl(3,4-methylenedioxy-phenyl)acetate (3.9 g, 21.2 mMol) and the mixture was refluxed for 2.5 h. The reaction was cooled and filtered. The filtrate was concentrated in vacuo and the residue was purified by flash chromatography on silica-gel using 10% ethyl acetate-hexane. Yield 2.6 g (oil).

¹H-NMR (400 MHz, CDCl₃, ppm): δ 7.105 (d, 1H), 6.93 (d, 1H), 6.72 (m, 1H), 5.964 (s, 2H), 5.28 (s, 1H), 3.76 (s, 3H).

Step B: Preparation of 4-(1-carbomethoxy-1-(3,4-methylenedioxy phenyl)methoxy)-3,5-dipropylbenzylalcohol To a solution of (3,5-dipropyl-4-hydroxy)benzyl alcohol (0.19 g, 1.0 mMol) in dry DMF (4 mL) were added cesium carbonate (0.33 g, 1.01 mMol) and methyl 2-bromo-2-(3,4-methylenedioxyphenyl)acetate (0.272 g, 1.0 mMol) and the mixture was stirred at room temperature for 3 h. At the end of this period, the reaction mixture was poured into ice water and extracted with ethyl acetate. The organic phase was washed with water, brine, dried (MgSO₄) and then filtered. The filtrate was concentrated in vacuo to provide an oil, which was then purified by flash chromatography on silica-gel using ethyl acetate-hexane (1:4) to provide the titled product as a thick colorless oil (0.30 g).

¹H-NMR (200 MHz, CDCl₃, ppm): δ 7.05 (s, 1H), 6.97 (s, 2H), 6.88 (d, 1H), 6.75 (d, 1H), 5.97 (s, 2H), 5.00 (s, 1H), 4.55 (s, 2H), 3.74 (s, 3H), 2.38 (m, 4H), 1.45 (m, 4H), 0.82 (t, 6H).

Step C: Preparation of 4-(1-carbomethoxy-1-(3,4-methylenedioxy-phenyl)methoxy)-3,5-dipropylbenzylbromide To a solution of the product of Step B (0.53 g, 1.38 mMol) in dry THF (10 mL) were added Ph₃P (0.49 g, 2.06 mMol), CBr₄ (0.69 g, 2.06 mMol) and CH₃CN (2 mL), and the mixture was stirred at room temperature for 14 h. At the end of this period, the reaction mixture was concentrated in vacuo to provide an oil, which was then purified by flash chromatography on silica-gel using ethyl acetate-hexane (1:9) to provide the titled product as a thick colorless oil (0.57 g).

¹H-NMR (400 MHz, CDCl₃, ppm): δ 7.04 (d, 1H), 7.00 (s, 2H), 6.87 (dd, 1H), 6.76 (d, 1H), 5.97 (s, 2H), 5.00 (s, 1H), 4.41 (s, 2H), 3.73 (s, 3H), 2.36 (m, 4H), 1.45 (m, 4H), 0.82 (t, 6H).

Step D: Preparation of 3-[4-(1-carbomethoxy-1-(3,4-methylenedioxy-phenyl)-methoxy)-3,5-dipropylphenyl-methyl]-2-methyl-3H-imidazo[4,5-b]pyridine Cesium carbonate (294 mg, 0.902 mmol) was added to 2-methylimidazo[4,5-b]pyridine (60 mg, 0.451 mmol) in DMF (2 mL) at room temperature under nitrogen. After stirring at 50° C. for 15 min, a solution of 4-(1-carbomethoxy-1-(3,4-methylenedioxyphenyl)methoxy)-3,5-dipropylbenzyl bromide (from Step C) (271 mg, 0.585 mmol) in DMF (2 mL) was added and the mixture stirred at 50° C. for 12 h. After cooling to room temperature, the mixture was poured onto ice/water and extracted with ethyl acetate (4 times). The combined organic phase was washed with water twice, brine, dried (magnesium sulfate) and the solvent removed in vacuo. The crude product (a mixture of regioisomers) was purified by flash chromatography on silica-gel (3,4,5% methanol/methylene chloride) to provide the title compound (87 mg).

¹H-NMR (400 MHz, CDCl₃, ppm): δ 8.31 (d, 1H), 7.95 (m, 1H), 7.19 (m, 1H), 7.00 (d, 1H), 6.81 (d, 1H), 6.75 (s, 2H), 6.72 (d, 1H), 5.94(s, 2H), 5.35 (s, 2H), 4.94 (s, 1H), 3.70 (s, 3H), 2.50 (s, 3H), 2.29(m, 4H), 1.35 (m, 4H), 0.75 (t, 6H).

Step B: Preparation of 3-[4-(1-carboxy-1-(3,4-methylenedioxyphenyl)methoxy)-3,5-dipropylphenylmethyl]-2-methyl-3H-imidazo[4,5-b]pyridine A 5N sodium hydroxide solution (0.4 mL) was added to a stirred mixture of the product of Step D (53.5 mg, 0.104 mmol) in methanol (4 mL). A few drops of methylene chloride were added to allow stirring then the mixture was stirred at room temperature for 2 h. The solution volume was reduced to ~10% in vacuo then 5% citric acid solution was added. The mixture was extracted with ethyl acetate (3 times). The combined organic phase was washed with water, brine, dried (magnesium sulfate) and the solvent removed in vacuo. The residue was chromatographed (8, 10% methanol/methylene chloride) to give the titled compound (28.5 mg) as a white solid.

¹H-NMR (400 MHz, CD₃OD, ppm): δ 8.33 (d, 1H) 7.98 (m, 1H), 7.31 (dd, 1H), 6.98 (d, 1H), 6.80 (m, 3H), 6.69 (m, 1H), 5.91 (s, 2H), 5.44 (s, 2H), 4.83 (s, 1H), 2.52 (s, 3H), 2.30 (m, 4H), 1.42 (m, 2H), 1.29 (m, 2H), 0.75 (t, 6H).

FAB-MS: m/e 540.8 (M+K).

EXAMPLE 19

1-[4-(1-carboxy-1-(3,4-methylenedioxyphenyl)methoxy)-3,5-dipropylphenylmethyl]-2-methyl-1H-imidazo[4,5-b]pyridine Step A: Preparation of 1-[4-(1-carbomethoxy-1-(3,4-methylenedioxy-phenyl)methoxy)-3,5-dipropylphenylmethyl]-2-methyl-1H-imidazo[4,5-b]pyridine The titled compound, 1-[4-(1-carbomethoxy-1-(3,4-methylenedioxyphenyl)methoxy)-3,5-dipropylphenylmethyl]-2-methyl-1H-imidazo[4,5-b]pyridine (38 mg), was isolated from the crude product obtained in Step D of Example 18.

¹H-NMR (400 MHz, CDCl₃, ppm): δ 8.47 (m, 1H), 7.45 (d, 1H), 7.10 (m, 1H), 6.99 (d, 1H), 6.81 (d, 1H), 6.72 (d, 1H), 6.63 (s, 2H), 5.95 (s, 2H), 5.19 (s, 2H), 4.96 (s, 1H), 3.71 (s, 3H), 2.60 (s, 3H), 2.30 (m, 4H), 1.36 (m, 4H), 0.75 (t, 6H).

Step B: Preparation of 1-[4-(1-carboxy-1-(3,4-methylenedioxyphenyl)methoxy)-3,5-dipropylphenylmethyl]-2-methyl-1H-imidazo[4,5-b]pyridine A 5N sodium hydroxide solution (0.2 mL) was added to a stirred mixture of the product of Step A (27 mg, 0.0524 mmol) in methanol (2 mL). A few drops of methylene chloride were added to allow stirring then the mixture was stirred at room temperature for 2 h. The solution volume was reduced to ~10% in vacuo then 5% citric acid solution added. The mixture was extracted with ethyl acetate (3 times). The combined organic phase was washed with water, brine, dried (magnesium sulfate) and the solvent removed in vacuo. The residue was purified by flash-chromatography using silica gel (8, 10% methanol/methylene chloride) to give the titled compound (12.8 mg) as a white solid.

$^1$H-NMR (400 MHz, CD$_3$OD, ppm): δ 8.36 (d, 1H), 7.85 (d, 1H), 7.26 (m, 1H), 6.98 (s, 1H), 6.78 (m, 3H), 6.69 (d, 1H), 5.91 (s, 2H), 5.40 (s, 2H), 4.82 (s, 1H), 2.62 (s, 3H), 2.32 (m, 4H), 1.44 (m, 2H), 1.29 (m, 2H), 0.75 (t, 6H).

FAB-MS: m/e 540.7 (M+K).

EXAMPLE 20

3-[4-(1-Carboxy-1-(3,4-methylenedioxyphenyl)methoxy)-3,5-dipropylphenylmethyl]-4-chloro-3H-imidazo[4,5-c]pyridine Step A: Preparation of 3-[4-(1-carbomethoxy-1-(3,4-methylenedioxy-phenyl)methoxy)-3,5-dipropylphenylmethyl]-4-chloro-3H-imidazo[4,5-c]pyridine Cesium carbonate (117.3 mg, 0.36 mmol) was added to 4-chloroimidazo[4,5-c]pyridine (25 mg, 0.18 mmol) in DMF (2 mL) at room temperature under nitrogen. After stirring for 15 min, a solution of 4-(1-carbomethoxy-1-(3,4-methylenedioxyphenyl)methoxy)-3,5-dipropylbenzyl bromide (106.5 mg, 0.23 mmol) in DMF (2 mL) was added and the mixture stirred at room temperature for 12 h. The mixture was poured onto ice/water and the crude product that precipitated was collected by filtration. The crude material was pre-adsorbed on silica gel and chromatographed (0 to 50% hexane/ethyl acetate) to afford the title compound (25 mg).

$^1$H-NMR (CDCl$_3$): δ 8.24 (d, 1H), 8.00 (s, 1H), 7.68 (d, 1H), 7.04 (s, 1H), 6.88 (d, 1H), 6.82 (s, 2H), 6.75 (d, 1H), 5.96 (s, 2H), 5.60 (s,2H), 5.00 (s, 1H), 3.71 (s,3H), 2.35 (m, 4H), 1.40 (m, 4H), 0.78 (t, 6H).

Step B: Preparation of 3-[4-(1-carboxy-1-(3,4-methylenedioxyphenyl)methoxy)-3,5-dipropylphenylmethyl]-4-chloro-3H-imidazo[4,5-c]pyridine A 5N sodium hydroxide solution (0.1 mL) was added to a stirred mixture of the product of Step A (25 mg, 0.0466 mmol) in methanol (1 mL). A few drops of methylene chloride were added to allow stirring then the mixture was stirred at room temperature for 3 h. The solvent was removed in vacuo then 5% citric acid solution added. The precipitate was filtered off, washed with water and dried in vacuo to give the titled compound (20 mg).

$^1$H-NMR (400 MHz, CDCl$_3$, ppm): δ 8.22 (d, 1H), 8.01 (s, 1H), 7.68 (d, 1H), 6.99 (s, 1H), 6.86 (d, 1H), 6.81 (s, 2H), 6.75 (d, 1H), 5.95 (s, 2H), 5.60 (s, 2H), 5.05 (s, 1H), 2.35 (m, 4H), 1.40 (m, 4H), 0.78 (t, 6H).

FAB-MS: m/e 522.8 (M+H).

EXAMPLE 21

1-[4-(1-Carboxy-1-(3,4-methylenedioxyphenyl)methoxy)-3,5-dipropylphenylmethyl]-4-chloro-3H-imidazo[4,5-c]pyridine Step A: Preparation of 1-[4-(1-carbomethoxy-1-(3,4-methylenedioxy-phenyl)methoxy)-3,5-dipropylphenylmethyl]-4-chloro-3H-imidazo[4,5-c]pyridine The titled compound (59 mg) was isolated from the crude product obtained in Step A of Example 20.

$^1$H-NMR (400 MHz, CDCl$_3$, ppm): δ 8.16 (d, 1H), 8.00 (s, 1H), 7.15 (d, 1H), 7.00 (s, 1H), 6.85 (d, 1H), 6.78 (s, 2H), 6.75 (d, 1H), 5.95 (s, 2H), 5.25 (s,2H), 4.99 (s, 1H), 3.71 (s,3H), 2.34 (m, 4H), 1.42 (m, 4H), 0.78 (t, 6H).

Step B: Preparation of 1-[4-(1-carboxy-1-(3,4-methylenedioxyphenyl)methoxy)-3,5-dipropylphenylmethyl]-4-chloro-3H-imidazo[4,5-c]pyridine A 5N sodium hydroxide solution (0.1 mL) was added to a stirred mixture of the product of Step A (22 mg, 0.0410 mmol) in methanol (1mL). A few drops of methylene chloride were added to allow stirring then the mixture was stirred at room temperature for 2.5 h. The solvent was removed in vacuo then 5% citric acid solution added. The precipitate was filtered off, washed with water and dried in vacuo to give the titled carboxylic acid (18 mg).

$^1$H-NMR (400 MHz, CDCl$_3$, ppm): δ 8.18 (d, 1H), 8.02 (s, 1H), 7.15 (d, 1H), 6.99 (s, 1H), 6.85 (d, 1H), 6.81 (s, 2H), 6.75 (d, 1H), 5.97 (s, 2H), 5.25 (s, 2H), 5.06 (s, 1H), 2.35 (m, 4H), 1.42 (m, 4H), 0.78 (t, 6H).

FAB-MS: m/e 522.7 (M+H).

EXAMPLE 22

3-[4-(1-carboxy-1-(3,4-methylenedioxyphenyl)-methoxy)-3,5-dipropylphenylmethyl]-3H-imidazo[4,5-c]pyridine Step A: Preparation of 3-[4-(1-carbomethoxy-1-(3,4-methylenedioxy-phenyl)-methoxy)-3,5-dipropylphenyl]methyl-3H-imidazo[4,5-c]pyridine Cesium carbonate (156 mg, 0.48 mmol) was added to imidazo[4,5-c]pyridine (28.6 mg, 0.24 mmol) in DMF (3 mL) at room temperature under nitrogen. After stirring for 15 min, a solution of 4-(1-carbomethoxy-1-(3,4-methylenedioxyphenyl)-methoxy)-3,5-dipropylbenzyl bromide (121 mg, 0.26 mmol) in DMF (3 mL) was added and the mixture stirred at 50° C. for 18 h. The mixture was poured onto ice/water and extracted with ethyl acetate (3×30 mL). The combined organic phase was washed with water, brine, dried (magnesium sulfate) and the solvent removed in vacuo. The crude material was purified by flash column chromatography (0 to 5% methanol/methylene chloride) to afford the less polar isomer of the titled compound (19 mg).

$^1$H-NMR (400 MHz, CDCl$_3$, ppm): δ 8.92 (s, 1H), 8.48 (d, 1H), 8.23 (s, 1H), 7.91 (s, 1H), 7.02 (s, 1H), 6.86 (d, 1H), 6.84 (s, 2H), 6.75 (d, 1H), 5.95 (s, 2H), 5.38 (s,2H), 4.99 (s, 1H), 3.71 (s, 3H), 2.35 (m, 4H), 1.40 (m, 4H), 0.78 (t, 6H).

Step B: Preparation of 3-[4-(1-carboxy-1-(3,4-methylenedioxyphenyl)-methoxy)-3,5-dipropylphenylmethyl]-3H-imidazo[4,5-c]pyridine A 5N sodium hydroxide solution (0.1 mL) was added to a stirred mixture of the product of Step A (19 mg, 0.038 mmol) in methanol (1 mL). A few drops of methylene chloride were added to allow stirring then the mixture was stirred at room temperature for 3 h. The solvent was removed in vacuo then 5% citric acid solution added. The mixture was extracted with ethyl acetate (3×30 mL), washed water, brine, dried (magnesium sulfate), and the solvent was removed in vacuo to give the titled compound (14 mg).

$^1$H-NMR (400 MHz, CD$_3$OD, ppm): δ 8.98 (s, 1H), 8.75 (s,1H), 8.46 (s, 1H), 7.96 (d, 1H), 7.05 (s, 2H), 7.00 (s, 1H), 6.85 (d, 1H), 6.78 (d, 1H), 5.96 (s, 2H), 5.52 (s, 2H), 5.00 (s,1H), 3.71 (s, 3H), 2.40 (m, 4H), 1.46 (m, 4H), 0.80 (t, 6H).

FAB-MS: m/e 488.7 (M+H).

EXAMPLE 23

1-[4-(1-Carboxy-1-(3,4-methylenedioxyphenyl)-methoxy)-3,5-dipropylphenylmethyl]-3H-imidazo[4,5-c]pyridine Step A: Preparation of 1-[4-(1-carbomethoxy-1-(3,4-methylenedioxyphenyl)-methoxy)-3,5-dipropylphenylmethyl]-3H-imidazo[4,5-c]pyridine The titled compound was obtained in Step A of Example 22 as the more polar isomer (30 mg).

$^1$H-NMR (400 MHz, CDCl$_3$, ppm): δ 9.16 (s, 1H), 8.50 (d, 1H), 8.18 (s, 1H), 7.50 (d, 1H), 7.01 (s, 1H), 6.86 (d, 1H), 6.80 (s, 2H), 6.75 (d, 1H), 5.96 (s, 2H), 5.34 (s, 2H), 4.99 (s,1H), 3.71 (s, 3H), 2.35 (m, 4H), 1.45 (m, 4H), 0.78 (t, 6H).

Step B: Preparation of 1-[4-(1-carboxy-1-(3,4-methylenedioxyphenyl)-methoxy)-3,5-dipropylphenylmethyl]-3H-imidazo[4,5-c]pyridine A 5N sodium hydroxide solution (0.15 mL) was added to a stirred mixture of the ester, obtained in Step A, (29 mg, 0.058 mmol) in methanol (1.5 mL). A few drops of methylene chloride were added to allow stirring then the mixture was stirred at room temperature for 3 h. The solvent was removed in vacuo then 5% citric acid solution added. The precipitate was filtered off, washed with water and dried in vacuo to give the titled carboxylic acid (19 mg).

$^1$H-NMR (400 MHz, CDCl$_3$/CD$_3$OD, ppm): δ 9.02 (s, 1H), 8.49 (s, 1H), 8.36 (d, 1H), 7.65 (d, 1H), 6.98 (s, 1H), 6.94 (s, 2H), 6.84 (d, 1H), 6.75 (d, 1H), 5.94 (s, 2H), 5.43 (s, 2H), 4.95 (s,1H), 2.36 (t, 4H), 1.41 (m, 4H), 0.78 (t, 6H).

FAB-MS: m/e 488.7 (M+H).

EXAMPLE 24

3-[4-(1-(3,4-Methylenedioxyphenyl)-1-phenylsulfonylaminocarbonyl)methoxy)-3,5-dipropylphenylmethyl]-5,7-dimethyl-2-ethyl-3H-imidazo-[4,5-b]pyridine Step A: Preparation of 3-[4-(1-(3,4-methylenedioxyphenyl)-1-phenyl-sulfonylaminocarbonyl)methoxy)-3,5-dipropylphenylmethyl]-5,7-dimethyl-2-ethyl-3H-imidazo[4,5-b]pyridine A 15 mL capacity high pressure vessel equipped with a magnetic stir bar was charged with a solution of 0.400 g (0.74 mmol) of the product of Example 13 in 5.0 mL of anhydrous THF and 0.300 g (1.85 mmol) of 1,1'-carbonyldiimidazole was added. The vessel was sealed and the contents were stirred and heated at 80° C. for 2 hours. The reaction was then cooled to room temperature, opened and a solution of 0.290 g (1.84 mmol) of benzenesulfonamide and 275 μL (1.84 mmol) of 1,8-diazabicyclo[5.4.0]undec-7-ene in 5 mL THF was added. The reaction vessel was resealed and then stirred and heated at 80° C. overnight. The reaction vessel was then cooled, opened and the contents were partitioned between water and EtOAc. The organic layer was separated washed with 10% aqueous NaHSO$_4$, brine, dried (MgSO$_4$), filtered and evaporated. The residual oil was purified on a silica gel flash chromatography column eluted with 25% acetone/CHCl$_3$ which afforded after evaporation of the purified fractions 0.220 g (44%) of the title compound.

$^1$H NMR (400 MHz, CD$_3$OD, ppm): δ 0.64 (t, J=7.60 Hz, 6H), 1.19 (t, J=7.60 Hz, 3H), 1.15–1.26 (m, 2H), 1.28–1.38 (m, 2H), 2.10–2.19 (m, 4H), 2.56 (s, 3H), 2.60 (s, 3H), 2.82 (q, J=7.60 Hz, 2H), 4.80 (s, 1H), 5.42 (s, 2H), 5.94 (s, 2H), 6.71 (s, 2H), 6.73 (s, 2H), 6.79 (s, 1H), 7.02 (s, 1H), 7.46–7.60 (m, 3H), 7.78–7.81 (m, 2H).

FAB-MS: m/e 683 (M+1).

EXAMPLE 25

3-4-(1-(3,4-Methylenedioxyphenyl)-1-(thiophene-2-yl)sulfonylaminocarbonyl)methoxy)-3,5-dipropylphenylmethyl]-5,7-dimethyl-2-ethyl-3H-imidazo[4,5-b]pyridine Step A: Preparation of 3-[4-(1-(3,4-methylenedioxyphenyl)-1-(thiophene-2-yl)sulfonylaminocarbonyl)methoxy)-3,5-dipropylphenylmethyl]-5,7-dimethyl-2-ethyl-3H-imidazo-[4,5-b]pyridine A 15 mL capacity high pressure vessel equipped with a magnetic stir bar was charged with a solution of 0.230 g (0.42 mmol) of the product of Example 13 in 4.0 mL of anhydrous THF and 0.172 g (1.06 mmol) of 1,1'-carbonyldiimidazole was added. The vessel was sealed and the contents were stirred and heated at 80° C. for 2.5 hours. The reaction was then cooled to room temperature, opened and a solution of 0.172 g (1.06 mmol) of thiophene-2-ylsulfonamide and 158 μL (1.06 mmol) of 1,8-diazabicyclo[5.4.0]undec-7-ene in 4 mL THF was added. The reaction vessel was resealed and then stirred and heated at 80° C. overnight. The reaction vessel was then cooled, opened and the contents were partitioned between water and EtOAc. The organic layer was separated washed with 10% aqueous NaHSO$_4$, brine, dried (MgSO$_4$), filtered and evaporated. The residual oil was purified on a silica gel flash chromatography column eluted first with 250 mL of CHCl$_3$/MeOH/NH$_4$OH (95:5:0.5), next with 200 mL of CHCl$_3$/MeOH/NH$_4$OH (92:8:0.5), and finally with 200 mL of CHCl$_3$/MeOH/NH$_4$OH (90:10:0.5). Evaporation of the purified fractions and drying in vacuo afforded 0.104 g (36%) of the title compound.

$^1$H NMR (400 MHz, CD$_3$OD, ppm): δ 0.67 (t, J=7.60 Hz, 6H), 1.19 (t, J=7.60 Hz, 3H), 1.16–1.40 (m, 4H), 2.16–2.28 (m, 4H), 2.56 (s, 3H), 2.59 (s, 3H), 2.82 (q, J=7.60 Hz, 2H), 4.78 (s, 1H), 5.41 (s, 2H), 5.90 (s, 2H), 6.66 (d, J=8.00 Hz, 1H, 6.70–6.74 (m, 3H), 6.93 (d, J=1.60 Hz, 1H), 6.87–6.99 (m, 1H), 7.00 (s, 1H), 7.54–7.58 (m, 2H).

FAB-MS: m/e 689 (M+1).

EXAMPLE 26

3-[4-(1-(4-Isobutylthiophene-2-yl)sulfonylaminocarbonyl)-1-(3,4-methylenedioxyphenyl)methoxy)-3,5-dipropylphenylmethyl]-5,7-dimethyl-2-ethyl-3H-imidazo[4,5-b]pyridine Step A: Preparation of 3-[4-(1-(4-isobutylthiophene-2-yl)sulfonylaminocarbonyl)-1-(3,4-methylenedioxyphenyl)methoxy)-3,5-dipropylphenylmethyl]-5,7-dimethyl-2-ethyl-3H-imidazo-[4,5-b]pyridine A 15 mL capacity high pressure vessel equipped with a magnetic stir bar was charged with a solution of 0.230 g (0.42 mmol) of the product of Example 13 in 4.0 mL of anhydrous THF and 0.172 g (1.06 mmol) of 1,1'-carbonyldiimidazole was added. The vessel was sealed and the contents were stirred and heated at 80° C. for 2 hours. The reaction was then cooled to room temperature, opened and a solution of 0.213 g (1.06 mmol) of 4-isobutylthiophene-2-ylsulfonamide and 158 μL (1.06 mmol) of 1,8-diazabicyclo[5.4.0]undec-7-ene in 4 mL THF was added. The reaction vessel was resealed and then stirred and heated at 80° C. overnight. The reaction vessel was then cooled, opened and the contents were partitioned between water and EtOAc. The organic layer was separated washed with 10% aqueous NaHSO$_4$, brine, dried (MgSO$_4$), filtered and evaporated. The residual oil was purified on a silica gel flash chromatography column eluted first with 500 mL 50% EtOAc-hexane followed by 500 mL 25% acetone/CHCl$_3$. The product containing fractions were combined, evaporated and rechromatographed on a silica gel flash chromatography column eluted first with 250 mL of CHCl$_3$/MeOH/NH$_4$OH (95:5:0.5), next with 200 mL of CHCl$_3$/MeOH/NH$_4$OH (92:8:0.5), and finally with 200 mL of CHCl$_3$/MeOH/NH$_4$OH (90:10:0.5). Evaporation of the purified fractions and drying in vacuo afforded 0.047 g (15%) of the title compound.

$^1$H NMR (400 MHz, CD$_3$OD, ppm): δ 0.68 (t, J=7.60 Hz, 6H), 0.92 (d, J=6.40 Hz, 6H), 1.20 (t, J=7.60 Hz, 3H), 1.20–1.40 (m, 4H), 1.85 (m, J=6.40 Hz, 1H), 2.14–2.26 (m, 4H), 2.57 (s, 3H), 2.60 (s, 3H), 2.69 (d, J=7.20 Hz, 2H), 2.82 (q, J=7.60 Hz, 2H), 4.81 (s, 1H), 5.42 (s, 2H), 5.94 (s, 2H), 6.70–6.76 (m, 4H), 6.77–6.79 (m, 1H), 6.87 (s, 1H), 7.02 (s, 1H), 7.55 (d, J=4.00 Hz, 1H).

FAB-MS: m/e 745 (M+1).

EXAMPLE 27

3-[4-(1-(Isopropylsulfonylaminocarbonyl)-1-(3,4-methylenedioxyphenyl)-methoxy)-3,5-dipropylphenylmethyl]-5,7-dimethyl-2-ethyl-3H-imidazo-[4,5-b]pyridine Step A: Preparation of 3-[4-(1-(isopropylsulfonylaminocarbonyl)-1-(3,4-methylenedioxyphenyl)-methoxy)-3,5-dipropylphenyl-methyl]-5,7-dimethyl-2-ethyl-3H-imidazo[4,5-b]pyridine A 15 mL capacity high pressure vessel equipped with a magnetic stir bar was charged with a solution of 0.230 g (0.42 mmol) of the product of Example 13 in 4.0 mL of anhydrous THF and 0.172 g (1.06 mmol) of 1,1'-carbonyldiimidazole was added. The vessel was sealed and the contents were stirred and heated at 80° C. for 4 hours. The reaction was then cooled to room temperature, opened and a solution of 0.130 g (1.06 mmol) of isopropylsulfonamide and 158 μL (1.06 mmol) of 1,8-diazabicyclo[5.4.0]undec-7-ene in 4 mL THF was added. The reaction vessel was resealed and then stirred and heated at 80° C. overnight. The reaction vessel was then cooled, opened and the contents were partitioned between water and EtOAc. The organic layer was separated washed with 10% aqueous NaHSO$_4$, brine, dried (MgSO$_4$), filtered and evaporated. The residual oil was purified on a silica gel flash chromatography column eluted first with 250 mL of CHCl$_3$/MeOH/NH$_4$OH (95:5:0.5), next with 200 mL of CHCl$_3$/MeOH/NH$_4$OH (92:8:0.5), and finally with 200 mL of CHCl$_3$/MeOH/NH$_4$OH (90:10:0.5). Evaporation of the purified fractions and drying in vacuo afforded 0.074 g (27%) of the title compound.

$^1$H NMR (400 MHz, CD$_3$OD, ppm): δ 0.76 (t, J=7.60 Hz, 6H), 1.16–1.45 (m, 13 H), 2.25–2.38 (m, 4H), 2.57 (s, 3H), 2.60 (s, 3H), 2.82 (q, J=7.60 Hz, 2H), 3.61 (s, J=7.40 Hz, 1H), 4.87 (s, 1H), 5.43 (s, 2H), 5.94 (s, 2H), 6.75 (d, J=8.00 Hz, 1H), 6.76 (s, 2H), 6.85 (dd, J=1.60, 8.00 Hz, 1H), 7.01 (s, 1H), 7.03 (d, J=1.60 Hz, 1H).

FAB-MS: m/e 649 (M+1).

EXAMPLE 28

3-[4-(1-(3,4-Methylenedioxyphenyl)-1-(tetrazol-5-yl)aminocarbonyl)methoxy)-3,5-dipropylphenylmethyl]-5,7-dimethyl-2-ethyl-3H-imidazo-[4,5-b]pyridine Step A: Preparation of 3-[4-(1-(3,4-methylenedioxyphenyl)-1-(tetrazol-5-yl)aminocarbonyl)methoxy)-3,5-dipropylphenylmethyl]-5,7-dimethyl-2-ethyl-3H-imidazo-[4,5-b]pyridine A 15 mL capacity high pressure vessel equipped with a magnetic stir bar was charged with a solution of 0.200 g (0.37 mmol) of the product of Example 13 in 1.0 mL of anhydrous DMF and 0.172 g (1.06 mmol) of 1,1'-carbonyldiimidazole was added. The vessel was sealed and the contents were stirred and heated at 80° C. for 1 hour. The reaction was then cooled to room temperature, opened and 0.063 g (0.74 mmol) of 5-aminotetrazole and 110 μL (0.74 mmol) of 1,8-diazabicyclo[5.4.0]undec-7-en was added. The reaction vessel was resealed and then stirred and heated at 80° C. for 3 hours. The reaction vessel was then cooled, opened and the contents were partitioned between water and EtOAc. The organic layer was separated washed with 10% aqueous NaHSO$_4$, brine, dried (MgSO$_4$), filtered and evaporated. The residual oil was purified on a silica gel flash chromatography column eluted first with 300 mL of 8% isopropanol/CH2Cl2, followed by 300 mL of CHCl$_3$-MeOH-NH$_4$OH (80:15:1). The product containing fractions were evaporated and dried in vacuo to afford 0.043 g of the title compound contaminated with some remaining starting material.

Step B: Tritylation of 3-[4-(1-(3,4-methylenedioxyphenyl)-1-(tetrazol-5-yl)aminocarbonyl)methoxy)-3,5-dipropylphenylmethyl]-5,7-dimethyl-2-ethyl-3H-imidazo[4,5-b]pyridine To a solution of 0.043 g (0.07 mmol) of the product of step A dissolved in 1 mL methylene chloride was added 0.020 g (0.07 mmol) of triphenylmethyl chloride, 20 μL (0.14 mmol) of triethylamine, and 0.5 mg of 4-dimethylaminopyridine. The reaction mixture was stirred at room temperature for 4 hours, then evaporated in vacuo. The residue was purified on a silica gel flash chromatography column eluted with 50% EtOAc-hexane, and the fractions containing a new less-polar product were separated, evaporated and dried in vacuo to afford 0.015 g of the title compound.

$^1$H NMR (400 MHz, CDCl$_3$, ppm): consistent with structure.

FAB -MS: m/e 853 (M+1).

Step C: Deprotection of N-tritylated 3-[4-(1-(3,4-methylenedioxyphenyl) -1-(tetrazol-5-yl)aminocarbonyl)methoxy)-3,5-dipropylphenylmethyl]-5,7-dimethyl-2-ethyl-3H-imidazo-[4,5-b]pyridine To a stirred solution of 0.015 g (0.02 mmol) of the product of step B dissolved in 0.2 mL ethanol was added 0.1 mL of 1N hydrochloric acid and the reaction mixture was stirred at room temperature for 2 hours. The reaction mixture was neutralized with 0.1 mL of 1N sodium hydroxide to pH=5, then concentrated in vacuo. The residue was purified on a silica gel flash chromatography column eluted with CHCl$_3$-MeOH-NH$_4$OH (80:15:1), the purified fractions were combined, evaporated, and dried in vacuo to afford 7 mg of the title compound free of the corresponding carboxylic acid.

$^1$H NMR (400 MHz, CD$_3$OD, ppm): δ 0.70 (t, J=7.60 Hz, 6H), 1.21 (t, J=7.60 Hz, 3H), 1.28–1.45 (m, 4H), 2.28–2.34 (m, 4H), 2.57 (s, 3H), 2.60 (s, 3H), 2.82 (q, J=7.60 Hz, 2H), 5.14 (s, 1H), 5.45 (s, 2H), 5.94–5.96 (m, 2H), 6.78 (d, J=8.00 Hz, 1H), 6.80 (s, 2H), 6.90 (dd, J=1.60, 8.00 Hz, 1H), 7.02 (s, 1H), 7.05 (d, J=1.60 Hz, 1H).

FAB-MS: m/e 611 (M+1).

EXAMPLE 29

3-[4-(1-Carboxy-1-(3,4-methylenedioxyphenyl)methoxy)-3,5-dichlorophenylmethyl]-5,7-dimethyl-2-ethyl-3H-imidazo[4,5-b]pyridine Step A: Preparation of ethyl 2-(2,6-dichloro-4-hydroxymethylphenoxy)-2-(3,4-methylene dioxyphenyl)acetate To a solution of 0.120 g (0.62 mmol) of 3,5-dichloro-4-hydroxybenzyl alcohol in 1.5 mL DMF was added 0.223 g (0.68 mmol) of cesium carbonate and the reaction was magnetically stirred at room temperature for 15 minutes. A solution of 0.196 g (0.68 mmol) of ethyl α-bromo-3,4-methylenedioxyphenylacetate in 0.5 mL DMF was added and the reaction was stirred an additional 30 minutes at room temperature. The reaction mixture was partitioned between EtOAc and 5% aqueous citric acid, extracted, dried (MgSO$_4$), filtered and evaporated. The residue was purified on a silica gel flash chromatography column eluted with 30% EtOAc-hexane, and evaporation of the purified fractions afforded 0.214 g (86%) of the title compound.

$^1$H NMR (200 MHz, CDCl$_3$, ppm): δ 1.25 (t, J=7.20 Hz, 3H), 4.15–4.31 (m, 2H), 4.61 (s, 2H), 5.68 (s, 1H), 5.98 (s, 2H), 6.75 (d, J=8.00 Hz, 1H), 6.93 (dd, J=1.60, 8.00 Hz, 1H), 7.09 (d, J=1.60 Hz, 1H), 7.26 (s, 2H).

FAB-MS: m/e 399 (M+1).

Step B: Preparation of ethyl 2-(4-bromomethyl-2,6-dichlorophenoxy)-2-(3,4-methylenedioxyphenyl)acetate To a magnetically stirred solution of 0.206 g (0.52 mmol) of the product of step A dissolved in 2 mL methylene chloride was added 0.162 g (0.62 mmol) of triphenylphosphine followed by 0.205 g (0.62 mmol) of carbon tetrabromide at 0° C. The reaction mixture was held at 0° C. for 10 minutes, then allowed to warm to room temperature and stirred for 2.5 hours. The reaction mixture was then concentrated in vacuo and the residue was applied to a silica gel flash chromatography column and eluted with 15% EtOAc-hexane. The purified fractions were combined, evaporated and dried in vacuo to afford 0.220 g (92%) yield of the title compound.

$^1$H NMR (200 MHz, CDCl$_3$, ppm): δ 1.24 (t, J=7.20 Hz, 3H), 4.15–4.32 (m, 2H), 4.33 (s, 2H), 5.70 (s, 1H), 5.97 (s, 2H), 6.76 (d, J=8.00 Hz, 1H), 6.94 (dd, J=1.60, 8.00 Hz, 1H), 7.10 (d, J=1.60 Hz, 1H), 7.28 (s, 2H).

FAB -MS: m/e 461 (M+1).

Step C: Preparation of 3-[4-(1-carboethoxy)-1-(3,4-methylenedioxyphenyl)methoxy)-3,5-dichlorophenylmethyl]-5,7-dimethyl-2-ethyl-3H-imidazo[4,5-b]pyridine To a solution of 0.034 g (0.20 mmol) of 5,7-dimethyl-2-ethylimidazo[4,5-b]pyridine in 0.5 mL anhydrous DMF was added 8.6 mg (0.22 mmol) of a 60% oil dispersion of sodium hydride and the reaction mixture was stirred under a nitrogen atmosphere at room temperature for 30 minutes. A solution of 0.100 g (0.22 mmol) of the product of Step B in 0.9 mL of DMF was added and the reaction was stirred an additional 1.5 hour at room temperature. The reaction mixture was partitioned between EtOAc and 5% aqueous NH$_4$Cl, separated, dried (MgSO$_4$), filtered and evaporated. The residue was purified on a silica gel flash chromatography column eluted with 50% EtOAc-hexane. Evaporation of the purified fractions and drying in vacuo afforded 0.081 g (74%) of the title compound.

$^1$H NMR (200 MHz, CDCl$_3$, ppm): δ 1.22 (t, J=7.60 Hz, 3H), 1.29 (t, J=7.40 Hz, 3H), 2.59 (s, 3H), 2.64 (s, 3H), 2.76 (q, J=7.60 Hz, 2H), 4.12–4.31 (m, 2H), 5.33 (s, 2H), 5.68 (s, 1H), 5.97 (s, 2H), 6.72 (d, J=8.00 Hz, 1H), 6.90 (dd, J=1.60, 8.00 Hz, 1H), 6.92 (s, 1H), 7.05 (s, 2H), 7.07 (d, J=1.60 Hz, 1H).

FAB-MS: m/e 556 (M+1).

Step D: Preparation of 3-[4-(1-carboxy-1-(3,4-methylenedioxyphenyl)methoxy)-3,5-dichlorophenyl-methyl]-5,7-dimethyl-2-ethyl-3H-imidazo[4,5-b]pyridine To a magnetically stirred solution of 0.076 g (0.14 mmol) of the product of Step C in 1.0 mL methanol was added 0.1 mL of a 5.0N solution of sodium hydroxide and the reaction was stirred at room temperature overnight. The reaction mixture was adjusted to pH=6 with 1.0N hydrochloric acid and then concentrated in vacuo. The residue was then purified on a silica gel flash chromatography column eluted with CHCl$_3$-MeOH—NH$_4$OH (80:15:1). Evaporation of the purified fractions and drying in vacuo afforded 0.059 g (82%) of the title compound.

$^1$H NMR (400 MHz, CD$_3$OD, ppm): δ 1.22 (t, J=7.60 Hz, 3H), 2.57 (s, 3H), 2.60 (s, 3H), 2.83 (q, J=7.60 Hz, 2H), 5.44 (s, 2H), 5.67 (s, 1H), 5.92–5.93 (m, 2H), 6.70 (d, J=8.00 Hz, 1H), 6.84 (dd, J=1.60, 8.00 Hz, 1H), 6.96 (d, J=1.60 Hz, 1H), 7.04 (s, 1H), 7.07 (s, 2H).

FAB-MS: m/e 528 (M+1).

EXAMPLE 30

3-[4-(1-Carboxy-1-(3,4-methylenedioxyphenyl)methoxy)-3-propylphenyl-methyl-]-5,7-dimethyl-2-ethyl-3H-imidazo[4,5-b]pyridine Step A: Preparation of 3-[4-(1-ethoxycarbonyl-1-(3,4-methylenedioxy-phenyl)methoxy)-3-propylphenylmethyl]-5,7-dimethyl-2-ethyl-3H-imidazo[4,5-b]pyridine To a solution of 0.257 g (0.80 mmol) of 5,7-dimethyl-2-ethyl-3-[4-hydroxy-3-propylphenyl]-methyl-3H-imidazo[4,5-b]pyridine in 4 mL of anhydrous DMF was added 0.309 g (0.88 mmol) of cesium carbonate and the mixture was stirred at room temperature for 15 minutes. Ethyl α-bromo-3,4-methylenedioxyphenylacetate (0.251 g; 0.88 mmol) was added and the reaction mixture was then stirred an additional 14 hours at room temperature. The reaction mixture was then partitioned between ethyl acetate and 10% aqueous citric acid and extracted. The organic layer was washed with saturated NaHCO$_3$, brine, dried (MgSO$_4$), filtered and evaporated. The residue was purified on a silica gel flash chromatography column eluted with 50% EtOAc-hexane. Evaporation of the purified fractions and drying in vacuo afforded 0.346 g (82%) of the title compound.

$^1$H NMR (400 MHz, CDCl$_3$, ppm): δ 0.90 (t, J=7.60 Hz, 3H), 1.14 (t, J=7.20 Hz, 3H), 1.27 (t, J=7.60 Hz, 3), 1.53–1.68 (m, 2H), 2.56–2.67 (m, 2H), 2.58 (s, 3H), 2.63 (s, 3H), 2.78–2.81 (m, 2H), 4.08–4.81 (m, 2H), 5.35 (s, 2H), 5.44 (s, 1H), 5.95 (br s, 2H), 6.57 (d, J=8.40 Hz, 1H), 6.77–6.80 (m, 2H), 6.89 (s, 1H), 6.96–6.99 (m, 2H), 7.02 (d, J=2.00 Hz, 1H).

FAB-MS: m/e 530 (M+1).

Step B: Preparation of 3-[4-(1-carboxy-1-(3,4-methylenedioxyphenyl)methoxy)-3-propylphenylmethyl]-5,7-dimethyl-2-ethyl-3H-imidazo[4,5-b]pyridine To a solution of 0.340 g (0.64 mmol) of the product of step A dissolved in 2 mL methanol was added 130 μL of a 5.0N solution of sodium hydroxide and the reaction mixture was stirred at room temperature for 2 hours. At this point the reaction mixture was adjusted to pH=6 with dropwise addition of 6.0N hydrochloric acid and the reaction mixture was concentrated in vacuo. The residue was applied to a silica gel flash chromatography column and eluted with CHCl₃-MeOH—NH₄OH (80:15:1). The purified fractions were combined, evaporated and dried in vacuo to afford 0.278 g (86%) of the title compound.

¹H NMR (400 MHz, CD₃OD, ppm): δ 0.84 (t, J=7.60 Hz, 3), 1.21 (t, J=7.60 Hz, 3H), 1.51–158 (m, 2H), 2.51–2.58 (m, 1H), 2.57 (s, 3H), 2.59 (s, 3H), 2.64–2.74 (m, 1H), 2.83 (q, J=7.60 Hz, 2H), 5.32 (s, 1H), 5.43 (s, 2H), 5.92 (br s, 2H), 6.76 (d, J=8.00 Hz, 2H), 6.85 (dd, J=2.40, 8.40 Hz, 1H), 6.93 (d, J=2.40 Hz, 1H), 7.00 (s, 1H), 7.04 (dd, J=1.60, 7.60 Hz, 1H), 7.08 (d, J=1.60 Hz, 1H).

FAB-MS: m/e 502 (M+1).

EXAMPLE 31

3-[4-(1-(4-(prop-2-yl)phenylsulfonylaminocarbonyl)-1-(3,4-methylenedioxyphenyl)methoxy)-3-propylphenyl-methyl]-5,7-dimethyl-2-ethyl-3H-imidazo[4,5-b]pyridine Step B: Preparation of 3-[4-(1-(4-(prop-2-yl)phenylsulfonylaminocarbonyl)-1-(3,4-methylenedioxyphenyl)-methoxy)-3-propyl-phenylmethyl]-5,7-dimethyl-2-ethyl-3H-imidazo-[4,5-b]-pyridine To a solution of 0.070 g (0.14 mmol) of the product of Step B in Example 30 dissolved in 1mL of anhydrous THF was added 0.034 g (0.21 mmol) of 1,1'-carbonyl-diimidazole and the mixture was refluxed under a nitrogen atmosphere for 20 minutes. The reaction was cooled to room temperature and opened and 31 μL of 1,8-diazabicyclo[5.4.0]undec-7-ene (DBU) and 0.042 g (0.21 mmol) of 4-iso-propylbenzenesulfonamide were added. The flask was resealed and the contents were stirred and heated at reflux for an additional 1.5 hours. The reaction mixture was then cooled and evaporated in vacuo. The residue was partitioned between EtOAc and 10% aqueous citric acid and the organic layer which separated was washed with saturated NaHCO₃, brine, dried (MgSO₄), filtered and evaporated. The residue was purified on a silica gel flash chromatography column eluted with CHCl₃-MeOH—NH₄OH (92:8:0.5). The purified fractions were combined, evaporated, and dried in vacuo to afford 0.040 g (42%) of the title compound.

¹H NMR (400 MHz, CD₃OD, ppm): δ 0.79 (t, J=7.60 Hz, 3H), 1.17 (d, J=7.20 Hz, 6H), 1.21 (t, J=7.60 Hz, 3H), 1.45–1.53 (m, 2H), 2.41–2.49 (m, 1H), 2.53–2.64 (m, 1H), 2.59 (s, 3H), 2.61 (s, 3H), 2.82 (q, J=7.60 Hz, 2H), 5.23 (s, 1H), 5.41 (s, 2H), 5.91 (br s, 2H), 6.57 (d, J=8.40 Hz, 1H), 6.72–6.76 (m, 2H), 6.91 (d, J=2.40 Hz, 1H), 6.59–6.97 (m, 2H), 7.02 (s, 1H), 7.15 (d, J=8.20 Hz, 2H), 7.63 (d, J=8.20 Hz, 2H).

FAB-MS: m/e 683 (M+1).

What is claimed is:

1. A compound of structural Formula I:

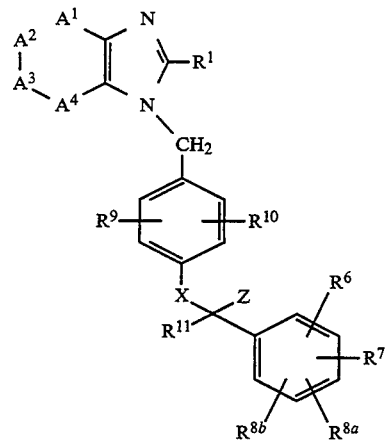

or a pharmaceutically acceptable salt thereof wherein:
R¹ is:
  (a) H,
  (b) (C₁–C₆)-alkyl, (C₂–C₆)-alkenyl or (C₂–C₆)-alkynyl each of which is unsubstituted or substituted with a substituent selected from the group consisting of:
    i) phenyl or naphthyl as defined in R¹(c),
    ii) (C₃–C₇)-cycloalkyl,
    iii) Cl, Br, I, F,
    iv) OH,
    v) NH₂,
    vi) NH(C₁–C₄)-alkyl,
    vii) N[(C₁–C₄)-alkyl)]₂,
    viii) NHSO₂R²,
    ix) (C₁–C₄)-perfluoroalkyl,
    x) COOR², or
    xi) SO₂NHR³,
    xii) —S(O)ₙ-(C₁–C₄)-alkyl, or
    xiii) —O—(C₁–C₄)-alkyl,
  (c) aryl, wherein aryl is defined as phenyl or naphthyl which is unsubstituted, mono- or disubstituted with substituents selected from the group consisting of:
    i) Cl, Br, I, F,
    ii) (C₁–C₄)-alkyl,
    iii) (C₁–C₄)-alkoxy,
    iv) NO₂,
    v) CF₃,
    vi) SO₂NR³R³,
    vii) (C₁–C₄)-alkylthio,
    viii) hydroxy,
    ix) amino,
    x) (C₃–C₇)-cycloalkyl, or
    xi) (C₃–C₁₀)-alkenyl,
  (d) heteroaryl, wherein heteroaryl is defined as a 5- or 6-membered heteroaromatic moiety selected from the group consisting of thiophene, furan, thiazole, oxazole, pyridine or pyrimidine, which is unsubstituted, mono- or disubstituted with substituents selected from the group consisting of:
    i) Cl, Br, I, F,
    ii) OH,
    iii) SH,
    iv) NO₂,
    v) (C₁–C₄)-alkyl,
    vi) (C₂–C₄)-alkenyl, vii) $(C_2-C_4)$-alkynyl,
viii) $(C_1-C_4)$-alkoxy, or
ix) $CF_3$,
(e) $(C_1-C_4)$-perfluoroalkyl,
(f) $-O-(C_1-C_6)$-alkyl,
(g) $-S(O)_n-(C_1-C_4)$-alkyl,
(h) $-CONR^3R^3$,
(i) $-NR^3CO-O(C_1-C_4)$-alkyl, or
(j) $(C_3-C_7)$-cycloalkyl; and
$-A^1-A^2-A^3-A^4-$ is:

(a) 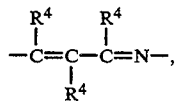

(b) 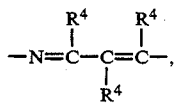

(c) 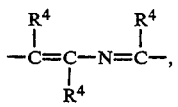

(d) 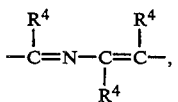

n is: 0 to 2; and
$R^2$ is:
(a) H, or
(b) $(C_1-C_6)$-alkyl; and
$R^3$ is:
(a) $R^2$,
(b) benzyl, or
(c) phenyl; and
$R^4$ groups are independently:
(a) H,
(b) $(C_1-C_6)$-alkyl or $(C_2-C_6)$-alkenyl each of which is unsubstituted or substituted with one of the following substituents,
  i) $-OH$,
  ii) $-O-(C_1-C_4)$-alkyl,
  iii) $-S(O)_n-(C_1-C_4)$-alkyl,
  iv) $-NR^5-(C_1-C_4)$-alkyl,
  v) $-NHR^5$,
  vi) $-COOR^5$,
  vii) $-CONHR^7$,
  ix) $-CONR^5R^{13}$, or
  x) $(C_3-C_7)$-cycloalkyl,
(c) $(C_3-C_7)$-cycloalkyl,
(d) F, Cl, Br, I,
(e) $CF_3$,
(f) $-COOR^5$,
(g) $-CONR^5R^{13}$,
(h) $-NR^5R^{13}$,
(i) $-NR^5CONR^5R^{13}$,
(j) $-NR^5COOR^{13}$,
(k) $-SO_2NR^5R^{13}$,
(l) $-O-(C_1-C_4)$-alkyl,
(m) $-S(O)_n-(C_1-C_4)$-alkyl, or
(n) $-NHSO_2R^{13}$; and
$R^5$ is:
(a) H,
(b) $(C_1-C_6)$-alkyl,
(c) aryl, wherein aryl is phenyl or naphthyl, which is unsubstituted or substituted as defined in $R^1(c)$,
(d) $-CH_2$-aryl, wherein aryl is phenyl or naphthyl, which is unsubstituted or substituted as defined in $R^1(c)$, or
(e) $(C_3-C_7)$-cycloalkyl; and
$R^6$ and $R^7$ on adjacent carbon atoms are joined together to form a ring structure:

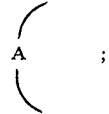

A represents:
(a) $-Y-[C(R^{12})(R^{12})]_s-Y-$; and
s is 1 or 2; and
Y is $-O-$, $-S(O)_n-$ and $NR^5$; and
$R^{8a}$ and $R^{8b}$ are independently:
(a) H,
(b) F, Cl, Br, or I,
(c) $-NO_2$,
(d) $-NH_2$,
(e) $-NH(C_1-C_4)$-alkyl,
(f) $-N[(C_1-C_4)$-alkyl$]_2$,
(g) $-SO_2NHR^5$,
(h) $-CF_3$,
(i) $(C_1-C_4)$-alkyl,
(j) $-OR^5$,
(k) $-S(O)n-(C_1-C_4)$-alkyl,
(l) $-NHCO-(C_1-C_4)$-alkyl,
(m) $-NHCO-O(C_1-C_4)$-alkyl,
(n) $-CH_2O-(C_1-C_4)$-alkyl,
(o) $-O-(CH_2)m-OR^5$,
(p) $-CONR^5R^{13}$, or
(q) $-COOR^5$; and
m is 2, 3, or 4; and
$R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^9$ and $R^{10}$ are on adjacent carbons, they can be joined to form a phenyl ring,
(h) perfluoro-$(C_1-C_6)$-alkyl,
(i) $(C_3-C_7)$-cycloalkyl, unsubstituted or substituted with $(C_1-C_6)$-alkyl,
(j) aryl, wherein aryl is phenyl or naphthyl,
(k) $(C_1-C_6)$-alkyl-$S(O)_n-(CH_2)_n-$,
(l) hydroxy-$(C_1-C_6)$-alkyl or dihydroxy-$(C_1-C_6)$-alkyl,
(m) $-CF_3$,
(n) $-CO_2R^5$,
(o) $-OH$,
(p) $-NR^5R^{13}$,
(q) $-[(C_1-C_6)$-alkyl$]NR^5R^{13}$,
(r) $-NO_2$,
(s) $-(CH_2)_n-SO_2-N(R^5)_2$,
(t) $-NR^5CO-(C_1-C_4)$-alkyl, or
(u) $-CON(R^5)_2$;
X is:
(a) $-O-$,
(b) $-S(O)_n-$,
(c) $-NR^5-$ (d) —CH₂O—,
(e) —CH₂S(O)ₙ,
(f) —CH₂NR⁵—,
(g) —OCH₂—,
(h) —NR⁵CH₂—,
(i) —S(O)ₙCH₂—, or
(j) single bond, R¹¹ is:
(a) H,
(b) (C₁-C₆)-alkyl, unsubstituted or substituted with a substituent selected from the group consisting of:
  (i) -aryl, wherein aryl is phenyl or naphthyl,
  (ii) -(C₃-C₇)-cycloalkyl,
  (iii) —NR⁵R¹³,
  (iv) -morpholin-4-yl,
  (v) —OH,
  (vi) —CO₂R⁵, or
  (vii) —CON(R⁵)₂,
(c) aryl, wherein aryl is phenyl or naphthyl, which is unsubstituted or substituted with a substituent selected from the group consisting of:
  i) (C₁-C₄)-alkyl,
  ii) —O—(C₁-C₄)-alkyl,
  iii) —CONR⁵R¹³,
  iv) F, Cl, Br or I, or
  v) —COOR⁵;

R¹² is:
(a) H,
(b) (C₁-C₄)-alkyl unsubstituted or substituted with one of the following substituents:
  i) —OH,
  ii) —NR⁵R¹³,
  iii) —COOR⁵,
  iv) —CONHR⁵, or
  v) —CONR⁵R¹³;

Z is:
(a) —CO₂H,
(b) —CO₂R¹⁴,
(c) -tetrazol-5-yl,
(d) —CONH(tetrazol-5-yl)
(e) —CONHSO₂-phenyl or —CONHSO₂-naphthyl, wherein phenyl or naphthyl is unsubstituted or substituted as defined in R¹(c),
(f) —CONHSO₂-(C₁-C₈)-alkyl, wherein the alkyl group is unsubstituted or substituted with a substituent selected from the group consisting of: —OH, —SH, —O(C₁-C₄)-alkyl, —S—(C₁-C₄)-alkyl, —CF₃, Cl, Br, F, I, —NO₂, —CO₂H, —CO₂-(C₁-C₄)-alkyl, —NH₂, —NH[(C₁-C₄)-alkyl], or —N[(C₁-C₄)-alkyl]₂,
(g) —CONHSO₂-(C₁-C₄)-perfluoroalkyl,
(h) —CONHSO₂-heteroaryl, wherein heteroaryl is as defined in R¹(d),
(i) —CONHSO₂NR³R³,
(j) —SO₂NHCO-phenyl or —SO₂NHCO-naphthyl, wherein phenyl or naphthyl is unsubstituted or substituted as defined in R¹(c),
(k) —SO₂NHCO-(C₁-C₈)-alkyl, wherein the alkyl group is unsubstituted or substituted with a substituent selected from the group consisting of: —OH, —SH, —O(C₁-C₄)-alkyl, —S—(C₁-C₄)-alkyl, —CF₃, Cl, Br, F, I, —NO₂, —CO₂H, —CO₂-(C₁-C₄)-alkyl, —NH₂, —NH[(C₁-C₄)-alkyl], —N[(C₁-C₄)-alkyl]₂,
(l) —SO₂NHCO-(C₁-C₄)-perfluoroalkyl,
(m) —SO₂NHCO-heteroaryl, wherein heteroaryl is as defined in R¹(d),
(n) —SO₂CONR³R³,
(o) —PO(OH)₂,
(p) —PO(OR²)₂, or
(q) —PO(OH)(OR²); and R¹³ is:
(a) H,
(b) (C₁-C₆)-alkyl,
(c) allyl,
(d) (C₃-C₆)-cycloalkyl,
(e) (C₁-C₄)-acyl,
(f) benzyl, or
(g) phenyl; and R¹⁴ is:
(a) (C₁-C₄)-alkyl,
(b) CHR¹⁵—O—COR¹⁶,
(c) CH₂CH₂—N[(C₁-C₂)-alkyl]₂,
(d) CH₂CH₂—N[CH₂CH₂]₂O,
(e) (CH₂CH₂O)ᵧ—O—[(C₁-C₄)-alkyl], wherein y is 1 or 2,
(f) phenyl, naphthyl, CH₂-phenyl or CH₂-naphthyl, where phenyl or naphthyl is substituted or unsubstituted with CO₂-(C₁-C₄)-alkyl,

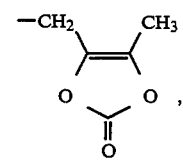
(g)

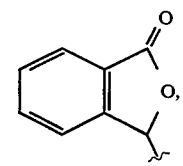
(h)

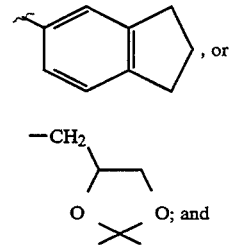
(i), or

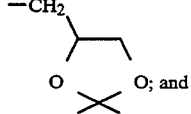
(j)

R¹⁵ and R¹⁶ independently are (C₁-C₆)-alkyl or phenyl.

2. The compound of claim 1 or a pharmaceutically acceptable salt thereof, wherein:
R¹ is:
(a) H,
(b) (C₁-C₆)-alkyl, (C₂-C₆)-alkenyl or (C₂-C₆)-alkynyl each of which is unsubstituted or substituted with a substituent selected from the group consisting of:
  i) (C₃-C₅)-cycloalkyl,
  ii) —O—(C₁-C₄)-alkyl,
  iii) —S—(C₁-C₄)-alkyl,
  iv) CF₃, or
  v) CF₂CF₃,
(c) (C₁-C₄)-perfluoroalkyl,
(d) —O—(C₁-C₆)-alkyl,
(e) —S(O)ₙ-(C₁-C₆)-alkyl,
(f) —CONR³R³, or
(g) —NR³CO—O(C₁-C₄)-alkyl;

—$A^1$—$A^2$—$A^3$—$A^4$— is:

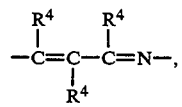 (a)

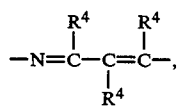 (b)

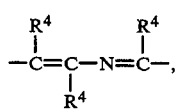 (c)

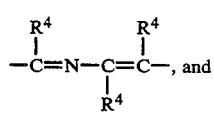, and (d)

n is: 0, 1, or 2; and
$R^2$ is:
  (a) H, or
  (b) ($C_1$–$C_6$)-alkyl; and
$R^3$ is:
  (a) $R^2$,
  (b) benzyl, or
  (c) phenyl; and
$R^4$ groups are independently:
  (a) H,
  (b) ($C_1$–$C_6$)-alkyl which is unsubstituted or substituted with one of the following substituents,
    i) —OH,
    ii) —O—($C_1$–$C_4$)-alkyl,
    iii) —S(O)$_n$-($C_1$–$C_4$)-alkyl,
    iv) —$NR^5$-($C_1$–$C_4$)-alkyl,
    v) —$NHR^5$,
    vi) —$COOR^5$,
    vii) —$CONHR^5$,
    viii) —$OCOR^{13}$,
    ix) —$CONR^5R^{13}$, or
    x) ($C_3$–$C_7$)-cycloalkyl,
  (c) ($C_3$–$C_7$)-cycloalkyl,
  (d) F, Cl, Br, I,
  (e) $CF_3$,
  (f) —$COOR^5$,
  (g) —$CONR^5R^{13}$,
  (h) —$NR^5R^{13}$,
  (i) —$NR^5CONR^5R^{13}$,
  (j) —$NR^5COOR^{13}$, or
  (k) —O—($C_1$–$C_4$)-alkyl; and
$R^5$ is:
  (a) H,
  (b) ($C_1$–$C_6$)-alkyl,
  (c) phenyl, or
  (d) benzyl; and
$R^6$ and $R^7$ on adjacent carbon atoms are joined together to form a ring structure:

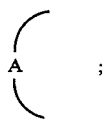

A represents:
  (a) —Y—[C($R^{12}$)($R^{12}$)]$_s$—Y—; and s is 1 or 2; and
Y is —O—, —S(O)$_n$— and $NR^5$; and
$R^{8a}$ and $R^{8b}$ are independently:
  (a) H,
  (b) F, Cl, Br, or I,
  (c) —$NO_2$,
  (d) ($C_1$–$C_4$)-alkyl,
  (e) —$OR^5$,
  (f) —S(O)$_n$-($C_1$–$C_4$)-alkyl,
  (g) —NHCO-($C_1$–$C_4$)-alkyl,
  (h) —NHCO-O($C_1$–$C_4$)-alkyl,
  (i) —O—($CH_2$)$_m$—$OR^5$,
  (j) —$CONR^5R^{13}$, or
  (k) —$COOR^5$; and
m is 2, 3, or 4; and
$R^9$ and $R^{10}$ are independently:
  (a) H,
  (b) ($C_1$–$C_6$)-alkyl, unsubstituted or substituted with ($C_3$–$C_7$)-cycloalkyl,
  (c) Cl, Br, F, I,
  (d) ($C_1$–$C_6$)-alkoxy, or
  (e) hydroxy-($C_1$–$C_6$)-alkyl or dihydroxy-($C_1$–$C_6$)-alkyl; and
X is:
  (a) —O—,
  (b) —S(O)$_n$—, or
  —$NR^5$—; and
$R^{11}$ is:
  (a) H,
  (b) ($C_1$–$C_6$)-alkyl, unsubstituted or substituted with:
    (i) -aryl, wherein aryl is phenyl or naphthyl,
    (ii) -($C_3$–$C_7$)-cycloalkyl,
    (iii) —$NR^5R^{13}$,
    (iv) -morpholin-4-yl,
    (v) —OH,
    (vi) —$CO_2R^5$, or
    (vii) —$CON(R^5)_2$,
  (c) aryl, wherein aryl is phenyl or naphthyl, which is unsubstituted or substituted with a substituent selected from the group consisting of:
    i) ($C_1$–$C_4$)-alkyl,
    ii) —O—($C_1$–$C_4$)-alkyl,
    iii) —$CONR^5R^{13}$,
    iv) F, Cl, Br or I, or
    v) —$COOR^5$;
$R^{12}$ is:
  (a) H,
  (b) ($C_1$–$C_4$)-alkyl unsubstituted or substituted with one of the following substituents:
    i) —OH,
    ii) —$NR^5R^{13}$,
    iii) —$COOR^5$,
    iv) —$CONHR^5$, or
    v) —$CONR^5R^{13}$;
Z is:
  (a) —$CO_2H$,
  (b) —$CO_2R^{14}$,
  (c) -tetrazol-5-yl,
  (d) —CONH(tetrazol-5-yl)
  (e) —$CONHSO_2$-phenyl or —$CONHSO_2$-naphthyl, wherein phenyl or naphthyl is unsubstituted or substituted as defined in $R^1$(c),
  (f) —$CONHSO_2$-($C_1$–$C_8$)-alkyl, wherein the alkyl group is unsubstituted or substituted with a substituent selected from the group consisting of: —OH, —SH, —O($C_1$–$C_4$)-alkyl, —S—($C_1$–$C_4$)-alkyl, —$CF_3$, Cl, Br, F, I, —$NO_2$, —$CO_2H$, —CO$_2$-(C$_1$-C$_4$)-alkyl, —NH$_2$, —NH[(C$_1$-C$_4$)-alkyl], or —N[(C$_1$-C$_4$)-alkyl]$_2$,
(g) —CONHSO$_2$-(C$_1$-C$_4$)-perfluoroalkyl,
(h) —CONHSO$_2$-heteroaryl, wherein heteroaryl is as defined in R$^1$(d),
(i) —CONHSO$_2$NR$^3$R$^3$,
(j) —SO$_2$NHCO-phenyl or —SO$_2$NHCO-naphthyl, wherein phenyl or naphthyl is unsubstituted or substituted as defined in R$^1$(c),
(k) —SO$_2$NHCO-(C$_1$-C$_8$)-alkyl, wherein the alkyl group is unsubstituted or substituted with a substituent selected from the group consisting of: —OH, —SH, —O(C$_1$-C$_4$)-alkyl, —S—(C$_1$-C$_4$)-alkyl, —CF$_3$, Cl, Br, F, I, —NO$_2$, —CO$_2$H, —CO$_2$-(C$_1$-C$_4$)-alkyl, —NH$_2$, —NH[(C$_1$-C$_4$)-alkyl], or —N[(C$_1$-C$_4$)-alkyl]$_2$,
(l) —SO$_2$NHCO-(C$_1$-C$_4$)-perfluoroalkyl,
(m) —SO$_2$NHCO-heteroaryl, wherein heteroaryl is as defined in R$^1$(d),
(n) —SO$_2$CONR$^3$R$^3$,
(o) —PO(OH)$_2$,
(p) —PO(OR$^2$)$_2$, or
(q) —PO(OH)(OR$^2$);

R$^{13}$ is:
(a) H,
(b) (C$_1$-C$_6$)-alkyl,
(c) allyl,
(d) (C$_3$-C$_6$)-cycloalkyl,
(e) (C$_1$-C$_4$)-acyl,
(f) benzyl, or
(g) phenyl;

R$^{14}$ is:
(a) (C$_1$-C$_4$)-alkyl,
(b) CHR$^{15}$—O—COR$^{16}$,
(c) CH$_2$CH$_2$—N[(C$_1$-C$_2$)-alkyl]$_2$,
(d) CH$_2$CH$_2$—N[CH$_2$CH$_2$]$_2$O,
(e) (CH$_2$CH$_2$O)$_y$—O—[(C$_1$-C$_4$)-alkyl], wherein y is 1 or 2,
(f) phenyl, naphthyl, —CH$_2$-phenyl or —CH$_2$-naphthyl, wherein phenyl or naphthyl is substituted or unsubstituted with CO$_2$-(C$_1$-C$_4$)-alkyl, (g) [structure]

(h) [structure]

(i) [structure], or (j) [structure]; and

R$^{15}$ and R$^{16}$ independently are (C$_1$-C$_6$)-alkyl or phenyl.

3. The compound of claim 2 of structural formula II

[structure II]

wherein,
R$^1$ is:
(a) H,
(b) (C$_1$-C$_6$)-alkyl,
(c) (C$_1$-C$_4$)-perfluoroalkyl,
(d) —O—(C$_1$-C$_6$)-alkyl, or
(e) —S(O)$_n$—(C$_1$-C$_6$)-alkyl; and
—A$^1$—A$^2$—A$^3$—A$^4$— is:

(a) [structure]

(b) [structure]

(c) [structure]

(d) [structure]

n is: 0, 1, or 2; and
R$^9$ and R$^{10}$ are each independently:
(a) (C$_1$-C$_6$)-alkyl,
(b) (C$_1$-C$_6$)-alkoxy,
(c) F, Cl, Br, I,
(d) (C$_1$-C$_6$)-alkyl-(C$_3$-C$_7$)-cycloalkyl, or
(e) hydroxy(C$_1$-C$_6$)-alkyl or dihydroxy(C$_1$-C$_6$)-alkyl; and X is:
(a) —O—, or
(b) NR$^5$;

Z is:
(a) —COOH,
(b) -tetrazol-5-yl,
(c) —CONH(5-tetrazolyl),
(d) —CONHSO$_2$—(C$_1$-C$_4$)-alkyl,
(e) —CONHSO$_2$—(C$_1$-C$_4$)-phenyl or —CONHSO2—(C1-C4)-naphthyl, wherein phenyl or naphthyl is unsubstituted or substituted as defined in R1(c), or (f) —CONHSO2—(C1-C4)-heteroaryl, wherein heteroaryl is as defined in R1(d).

4. The compound of claim 2 comprising the structural Formula III:

$$\text{III}$$

or a pharmaceutically acceptable salt thereof, wherein:

R1 is:
(a) H,
(b) (C1-C6)-alkyl, or
(c) (C1-C4)-perfluoroalkyl; and
—A1—A2—A3—A4— is:

(a) $-C(R^4)=C(R^4)-C(R^4)=N-$, (b) $-C(R^4)=C(R^4)-N=C(R^4)-$, (c) $-C(R^4)=N-C(R^4)=C(R^4)-$, or

R4 groups are independently:
(a) H,
(b) (C1-C6)-alkyl
(c) (C3-C7)-cycloalkyl,
(d) F, Cl, Br, I,
(e) CF3,
(f) —COOR5,
(g) —CONR5R13,
(h) —NR5R13,
(i) —NR5CONR5R13,
(j) —NR5COOR13, or
(k) —O—(C1-C4)-alkyl; and R6 and R7 on adjacent carbon atoms are joined together to form a ring structure:

A represents:
(a) —O—[C(R12)(R12)]s—O—;
s is 1 or 2; and
R8a and R8b are independently:
(a) H,
(b) F, Cl, Br, or I,
(c) —NO2,
(d) (C1-C4)-alkyl,
(e) —OR5,
(f) —S(O)n—(C1-C4)-alkyl,
(g) —NHCO—(C1-C4)-alkyl,
(h) —NHCO—O(C1-C4)-alkyl,
(i) —O—(CH2)m—OR5,
(j) —CONR5R13, or
(k) —COOR5; and
m is 2, 3, or 4; and
R12 is:
(a) H, or
(b) (C1-C4)-alkyl.

5. The compound of claim 1 of the structural formula wherein X is —O— and R7, R8a and R8b are H or as indicated in the table below:

| R1 | R4a | R4b | R9 | R10 | R6, R7, R8a, R8b | Z |
|---|---|---|---|---|---|---|
| Et | H | 7-Me | Pr | Pr | 2,3-methylenedioxy | COOH |
| Et | H | 7-Me | Pr | Pr | 3,4-methylenedioxy | COOH |
| Et | 5-Me | 7-Me | Pr | Pr | 3,4-methylenedioxy | CONHSO2Me |
| Et | H | 7-Me | Pr | Pr | 3,4-methylenedioxy | COOH |
| H | H | 7-Me | Pr | Pr | 3,4-methylenedioxy | COOH |
| Me | H | H | Pr | Pr | 3,4-methylenedioxy | COOH |
| Et | 5-Me | 7-Me | H | Pr | 3,4-methylenedioxy | CONHSO2Ph(4-iPr) |
| Et | H | H | H | Pr | 3,4-methylenedioxy | CONHSO2Ph(4-iPr) |
| H | H | H | Pr | Pr | 5-Br-3,4-methylenedioxy | COOH |
| H | 5-Me | 7-Me | Pr | Pr | 5-Br-3,4-methylenedioxy | COOH |
| H | H | H | Pr | H | 5-Br-3,4-methylenedioxy | COOH |

-continued

| $R^1$ | $R^{4a}$ | $R^{4b}$ | $R^9$ | $R^{10}$ | $R^6, R^7, R^{8a}, R^{8b}$ | Z |
|---|---|---|---|---|---|---|
| H | H | H | Pr | H | 5-Br-3,4-methylenedioxy | $CONHSO_2Ph(4\text{-}iPr)$ |
| Et | 5-Me | 7-Me | H | Pr | 3,4-methylenedioxy | $CONHSO_2Ph(4\text{-}tBu)$ |
| Et | 5-Me | 7-Me | H | —$CH_2$-c-Pr | 3,4-methylenedioxy | $CONHSO_2Ph(4\text{-}iPr)$ |
| H | H | H | H | Pr | 3,4-methylenedioxy | $CONHSO_2Ph(4\text{-}tBu)$ |
| H | H | H | H | —$CH_2$-c-Pr | 3,4-methylenedioxy | $CONHSO_2Ph(4\text{-}tBu)$. |

6. The compound of claim 1 of the structural formula

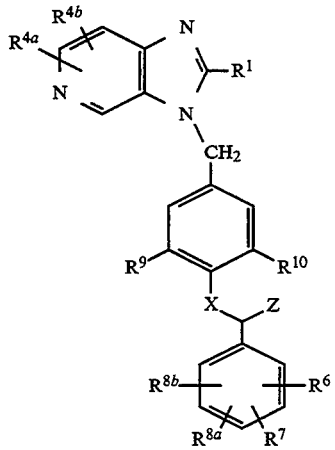

wherein X is —O— and $R^7$ is H, $R^{8a}$ and $R^{8b}$ are H or as indicated in the table below:

| $R^1$ | $R^{4a}$ | $R^{4b}$ | $R^9$ | $R^{10}$ | $R^6, R^7, R^{8a}, R^{8b}$ | Z |
|---|---|---|---|---|---|---|
| H | H | H | Pr | Pr | 3,4-methylenedioxy | COOH |
| Et | 5-Me | 7-Me | H | Pr | 3,4-methylenedioxy | $CONHSO_2Ph(4\text{-}iPr)$ |
| H | H | H | H | Pr | 3,4-methylenedioxy | $CONHSO_2Ph(4\text{-}iPr)$ |
| H | H | H | H | Pr | 3,4-methylenedioxy | $CONHSO_2Ph(4\text{-}tBu)$ |
| H | H | H | H | Pr | 3,4-methylenedioxy | $CONHSO_2Ph$ |
| Me | H | H | Pr | Pr | 3,4-methylenedioxy | COOH |
| Me | H | H | H | Pr | 3,4-methylenedioxy | COOH |
| Me | H | H | H | Pr | 3,4-methylenedioxy | $CONHSO_2Ph(4\text{-}iPr)$ |
| H | H | 7-SMe | Pr | Pr | 3,4-methylenedioxy | COOH |
| H | H | 7-$NMe_2$ | Pr | Pr | 3,4-methylenedioxy | COOH |
| H | H | H | Pr | Pr | 5-Br-3,4-methylenedioxy | COOH |
| Me | H | H | Pr | Pr | 5-Br-3,4-methylenedioxy | COOH. |

7. The compound of claim 1 of the structural formula

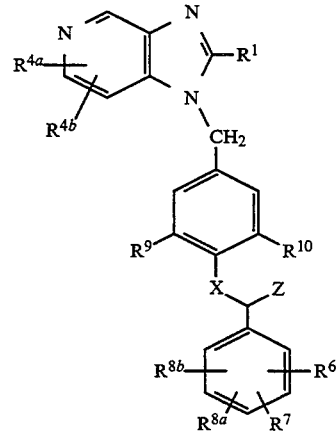

wherein X is —O— and $R^7$ is H, $R^{8a}$ and $R^{8b}$ are H or as indicated in the table below:

| $R^1$ | $R^{4a}$ | $R^{4b}$ | $R^9$ | $R^{10}$ | $R^6, R^7, R^{8a}, R^{8b}$ | Z |
|---|---|---|---|---|---|---|
| Me | 4-Cl | H | Br | Br | 2,3-methylenedioxy | COOH |
| Me | 4-Cl | H | Pr | Pr | 3,4-methylenedioxy | COOH |
| H | 4-Cl | H | Pr | Pr | 3,4-methylenedioxy | COOH |
| H | H | H | Pr | Pr | 3,4-methylenedioxy | COOH |
| H | H | H | Pr | H | 3,4-methylenedioxy | $CONHSO_2Ph(4\text{-}iPr)$. |

8. A pharmaceutical composition comprising a therapeutically effective amount of a compound of formula I as recited in claim 1 and a pharmaceutically acceptable carrier.

* * * * *